(12) United States Patent
Vicari et al.

(10) Patent No.: US 7,101,987 B2
(45) Date of Patent: Sep. 5, 2006

(54) CCL27 POLYPEPTIDES

(75) Inventors: Alain P. Vicari, Nancy (FR); Janine M. Morales, San Francisco, CA (US); Joseph A. Hedrick, Plainsboro, NJ (US); Albert Zlotnik, Palo Alto, CA (US)

(73) Assignee: Schering Corporation, Kenilworth, NJ (US)

( * ) Notice: Subject to any disclaimer, the term of this patent is extended or adjusted under 35 U.S.C. 154(b) by 574 days.

(21) Appl. No.: 10/146,496

(22) Filed: May 15, 2002

(65) Prior Publication Data

US 2003/0031646 A1    Feb. 13, 2003

Related U.S. Application Data

(63) Continuation-in-part of application No. 08/978,964, filed on Nov. 26, 1997, now abandoned.

(60) Provisional application No. 60/031,805, filed on Nov. 27, 1996, provisional application No. 60/032,606, filed on Dec. 5, 1996, provisional application No. 60/063,259, filed on Oct. 24, 1997.

(51) Int. Cl.
C07H 21/04    (2006.01)
C07K 1/00     (2006.01)
A01N 37/18    (2006.01)

(52) U.S. Cl. .......................... 536/23.5; 530/350; 514/2

(58) Field of Classification Search ................ None
See application file for complete search history.

(56) References Cited

FOREIGN PATENT DOCUMENTS

WO    WO 96/32481    10/1996

OTHER PUBLICATIONS

Wen D et al. Erythropoietin structure-function relationships: high degree of sequence homology among mammals. Blood. Sep. 1, 1993;82(5):1507-16.*
Mickle JE et al. Genotype-phenotype relationships in cystic fibrosis. Med Clin North Am. May 2000;84(3):597-607.*
Voet et al. Biochemistry. 1990. John Wiley & Sons, Inc. pp. 126-128 and 228-234.*
Yan et al., Two-amino acid molecular switch in an epithelial morphogen that regulates binding to two distinct receptors. Science 290: 523-527, 2000.*
Bacon and Schall, *Int Arch Allergy Immunol*, "Chemokines as mediators of allergic inflammation" 109(2):97-109 (1996).
Gronenborn and Clore, *Protein Eng*, "Modeling the three-dimensional structure of the monocyte chemo-attractant and activating protein MCAF/MCP-1 on the basis of the solution structure of interleukin-8" 4(3):263-269 (1991).
Hillier et al., *GenBank*, Accession No. R38459, May 4, 1995. "The WashU-Merck EST project".
Lodi et al., *Science*, "High-resolution solution structure of the β chemokine hMIP-1β by multidimensional NMR" 263(5154):1762-1767 (1994).
Marra et al., *GenBank*, Accession No. AA024054, Jan. 21, 1997. "The WashU-HHMI mouse EST project".
Marra et al., *GenBank*, Accession No. W82810, Sep. 12, 1996. "The WashU-HHMI mouse EST project".
Marra et al., *GenBank*, Accession No. W35071, Sep. 12, 1996. "The WashU-HHMI mouse EST project".
Marra et al., *GenBank*, Accession No. W10954, Sep. 5, 1996. "The WashU-HHMI mouse EST project".
Matsushima and Oppenheim, *Cytokine*. "Interleukin-8 and MCAF: novel inflammatory cytokines inducible by IL 1 and TNF" 1(1):2-13 (1989).
Miller and Krangel, *Proc Natl Acad Sci U S A.*, "The human cytokine I-309 is a monocyte chemoattractant" 89(7):2950-2954 (1992).
Oppenheim et al., *Annu Rev Immunol*. "Properties of the novel proinflammatory supergene 'intercrine' cytokine family" 9:617-648 (1991).
Sayle and Milner-White, *Trends Biochem Sci*, "RASMOL: biomolecular graphics for all" 20(9):374-376 (1995).
Schall and Bacon, *Curr Opin Immunol*, "Chemokines, leukocyte trafficking. and inflammation" 6(6):865-873 (1994).
Schall, *Cytokine*, "Biology of the RANTES/SIS cytokine family" 3(3): 165-183 (1991).
Stoeckle and Barker, *New Biol*, "Two-burgeoning families of platelet factor 4-related proteins: mediators of the inflammatory response" 2(4):313-323 (1990).
Thompson (Ed.), *The Cytokine Handbook*, 2nd ed., The Academic Press Inc.: San Diego, CA (1994).
Van Leuven et al., *GenBank*, Accession No. U32323, Nov. 22, 1996. "Molecular cloning and characterization of the human interleukin-11 receptor alpha-chain gene, IL11RA. located on chromosome 9p13".
*Derwent Geneseq Patent Sequence Database*, Accession No. 98P-W44397, citing: WO 9801557 A2, dated 980115; US 97-48593, dated 970604: US 96-675814, dated 960705; US 96-28329, dated 961011; "Search record pertaining to human VIC-1, performed on Jul. 6, 1998 and GWCC mouse, performed on Jul. 8, 1998".
*Derwent Geneseq Patent Sequence Database*, Accession No. 98P-W41938, citing: WO 9748807 A1, dated 971224; WO 96-US10561, dated 960617; "Search record pertaining to human VIC-1, performed on Jul. 6, 1998 and GWCC mouse. performed on Jul. 8, 1998".
*Derwent Geneseq Patent Sequence Database*, Accession No. 97P-W27271, citing: WO 9739126 A1, dated 971023; US 96-633682, dated 960417; "Search record pertaining to human VIC-1, performed on Jul. 6, 1998".

(Continued)

Primary Examiner—Robert S. Landsman
Assistant Examiner—Bruce D. Hissong

(57) ABSTRACT

Novel CC chemokines from human, reagents related thereto including purified proteins, specific antibodies and nucleic acids encoding these chemokines are provided. Also provided are methods of making and using said reagents and diagnostic kits.

9 Claims, 1 Drawing Sheet

OTHER PUBLICATIONS

*Derwent Geneseq Patent Sequence Database*, Accession No. 97P-W07606, citing: WO 9639522 A1, dated 961212; US 95-464401, dated 950605; US 95-460987, dated 950605; "Search record pertaining to human VIC-1, performed on Jul. 6, 1998 and GWCC mouse, performed on Jul. 8, 1998".

*Derwent Geneseq Patent Sequence Database*, Accession No. 96P-R97664, citing: WO 9617868 A, dated 960613; US 94-352324, dated 941207; "Search record pertaining to human VIC-1, performed on Jul. 6, 1998 and GWCC mouse, performed on Jul. 8, 1998".

*Derwent Geneseq Patent Sequence Database*, Accession No. 96P-W10574, citing: WO 9624668 A1, dated 960815; WO 95-US1780, dated 950208; ZA 95-1198, dated 950214; "Search record pertaining to human VIC-1, performed on Jul. 6, 1998 and GWCC mouse, performed on Jul. 8, 1998".

*Derwent Geneseq Patent Sequence Database*, Accession No. 98P-W44396. citing: WO 9801557 A2, dated 980115; US 97-48593 ,dated 970604; US 96-675814, dated 960705; US 96-28329, dated 61011: "Search record pertaining to human VIC-1, performed on Jul. 6, 1998".

*Derwent Geneseq Patent Sequence Database*, Accession No. 95P-R75752, citing: WO 9516048 A , dated 950615; US 93-164292, dated 931209; "Search record pertaining to human VIC-1, performed on Jul. 6, 1998".

*Derwent Geneseq Patent Sequence Database*. Accession No. 90P-R06416. citing: WO 9008188 A, dated 900726: AU 89-4860. dated 890623: AU 89-2220, dated 890110: AU 89-2706. dated 890213: "Search record pertaining to human VIC-1. performed on Jul. 6, 1998".

*Derwent Geneseq Patent Sequence Database*. Accession No. 88P-P80944. citing: WO 8801278 A, dated 880225: US 86-897245, dated 860818: "Search record pertaining to human VIC-1, performed on Jul. 6, 1998".

Database DGENE. Last updated Mar. 11, 1999, Result from sequence search using SEQ ID No. 2, Position Nos. 1-80. as the query and citing Accession Nos. 98P-W60649, 98P-W60651, 98P-W60652, 98P-W60650, 98P-W44397, 98P-W41938, 98P-W30565, 98P-W44396, 99P-W84157, 98P-W52842: Derwent Information Ltd., London.

Database DGENE. Last updated May 16, 1999. Result from sequence search using SEQ ID No. 2. Position Nos. 1-105. as the query and citing Accession Nos. 99P-W84157, 98P-W60652, 98P-W60651, 98P-W60650, 98P-W60649, 98P-W44397, 98P-W44396, 98P-W41938, 98P-W30565; Derwent Information Ltd., London.

Hillier et al., *GenBank*, Accession No. HS459102, May 6, 1995. yh89d12.41 "Homo sapiens cDNA clone 136919.5."

Marra et al., *GenBank*, Accession No. AA036506, Aug. 28, 1996. "The WashU-HHMI mouse EST project."

Harlow et al., "Antibodies: A Laboratory Manual," Chapter 5, p. 76, Cold Spring Harbor Laboratory, New York (1988).

George et al., "Macromolecular Sequencing & Synthesis," Chapter 12, pp. 127-149 Man R. Liss Inc., New York (1988).

Cunningham and Wells, *Science*, High-resolution epitope mapping of hGH-receptor interactions by alanine-scanning mutagenesis, 244(4908):1081-1085 (1989).

Van Leuven et al., *Genomics*, "Molecular cloning and characterization of the human interleukin-11 receptor alpha-chain gene, IL11RA, located on chromosome 9p13," 31(1):65-70 (1996).

Reiger et al., "Glossary of Genetics and Cytogenetics" 4th Edition, Springer-Verlag Publication, pp. 16-19 (1976).

Doerks et al., *Trends Genet*, "Protein Annotation: detective work for function prediction," 14(6): 248-250 (1998).

* cited by examiner

| | |
|---|---|
| hMCP-1  | MKVSAALLCLLLIAATFIPQGLAQPDAINAPVTCCYNF---TNRKISVQRLASY-RRITS |
| hMIP-3α | MCCTKSLLLAALMSVLLLHLCGESEA--ASNFDCCLGY--TDRILHPKFIVGFTRQLAN |
| hCCL28  | MQ-QRGLAIVALAVCAALHASEAILP---IASSCCTEVSHHISRRLLERVNMCR-IQRAD |
| hCCL27  | M-KGPPTFCSLLLSLLLSPDPTAAFLPPSTACCTQLYRKPLSDKLLRKVIQVELQEAD |
| mCCL27  | MMEGLSPASSLPLLLLLLSPAPEAALPLPSSTSCCTQLYRQPLPSRLLRRIVHMELQEAD |
| | * |

| | |
|---|---|
| hMCP-1  | SKCPKEAVIFKTIVAKEICADPK-----QKWVQDSMDHLDKQTQTPKT------- |
| hMIP-3α | EGCDINAIIFHTKKKLSVCANPK---QTWVKYIVRLLSKKVKDM---------- |
| hCCL28  | GDCDLAAVILHVKRRR-ICVSPHNHTVKQWMKVQAAKKNGKGNVCHRKKHGKRNSNRAH |
| hCCL27  | GDCHLQAFVLHLAQRS-ICIHPQNPSLSQWFEHQERKLHGTLPKLNFGMLRKMG---- |
| mCCL27  | GDCHLQAVVLHLARRS-VCVHPQNRSLARWLERQGKRLQGTVPSLNLVLQKKMYSNPQQQ |
| | * * * |

| | |
|---|---|
| hMCP-1  | ------- |
| hMIP-3α | ------- |
| hCCL28  | QGKHETYGHKTPY |
| hCCL27  | ------- |
| mCCL27  | N------ |

FIG. 1

SEQUENCE LISTING (1) GENERAL INFORMATION:

(iii) NUMBER OF SEQUENCES: 12

(2) INFORMATION FOR SEQ ID NO: 1:

(i) SEQUENCE CHARACTERISTICS:
    (A) LENGTH: 731 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: CDS
    (B) LOCATION: 56..436

(ix) FEATURE:
    (A) NAME/KEY: mat_peptide
    (B) LOCATION: 122..436

(ix) FEATURE:
    (A) NAME/KEY: misc_feature
    (B) LOCATION: 565
    (D) OTHER INFORMATION: /note= "nucleotides 565 and 581
        designated M, may be A or C"

(ix) FEATURE:
    (A) NAME/KEY: misc_feature
    (B) LOCATION: 712
    (D) OTHER INFORMATION: /note= "nucleotide 712 designated
        N, may be A, C, G, or T"

(xi) SEQUENCE DESCRIPTION: SEQ ID NO: 1:

```
GGCTGATCGA ACAGCCTCAC TTGTGTTGCT GTCAGTGCCA GTAGGGCAGG CAGGA ATG        58
                                                             Met
                                                             -22

CAG CAG AGA GGA CTC GCC ATC GTG GCC TTG GCT GTC TGT GCG GCC CTA        106
Gln Gln Arg Gly Leu Ala Ile Val Ala Leu Ala Val Cys Ala Ala Leu
    -20                 -15                 -10

CAT GCC TCA GAA GCC ATA CTT CCC ATT GCC TCC AGC TGT TGC ACG GAG        154
His Ala Ser Glu Ala Ile Leu Pro Ile Ala Ser Ser Cys Cys Thr Glu
 -5              1                5                  10

GTT TCA CAT CAT ATT TCC AGA AGG CTC CTG GAA AGA GTG AAT ATG TGT        202
Val Ser His His Ile Ser Arg Arg Leu Leu Glu Arg Val Asn Met Cys
             15                  20                  25
```

```
CGC ATC CAG AGA GCT GAT GGG GAT TGT GAC TTG GCT GCT GTC ATC CTT    250
Arg Ile Gln Arg Ala Asp Gly Asp Cys Asp Leu Ala Ala Val Ile Leu
         30                  35                  40

CAT GTC AAG CGC AGA AGA ATC TGT GTC AGC CCG CAC AAC CAT ACT GTT    298
His Val Lys Arg Arg Arg Ile Cys Val Ser Pro His Asn His Thr Val
     45                  50                  55

AAG CAG TGG ATG AAA GTG CAA GCT GCC AAG AAA AAT GGT AAA GGA AAT    346
Lys Gln Trp Met Lys Val Gln Ala Ala Lys Lys Asn Gly Lys Gly Asn
 60                  65                  70                  75

GTT TGC CAC AGG AAG AAA CAC CAT GGC AAG AGG AAC AGT AAC AGG GCA    394
Val Cys His Arg Lys Lys His His Gly Lys Arg Asn Ser Asn Arg Ala
             80                  85                  90

CAT CAG GGG AAA CAC GAA ACA TAC GGC CAT AAA ACT CCT TAT            436
His Gln Gly Lys His Glu Thr Tyr Gly His Lys Thr Pro Tyr
                 95                 100                 105

TAGAGAGTCT ACAGATAAAT CTACAGAGAC AATTCCTCAA GTGGACTTGG CCATGATTGG   496

TTGTCCTGCA TACTGATGAA ACTACTGATG TCVGCTGGTC TGAAAGGACC TACCAGAAGC   556

TAAATCTCMA AGAATGCCAT TTCCMTATCC CTAATGATTC AATCTCCCTT ACCCTGACCA   616

ATCAGTGGCC CAAATTTTCC AGCCCCTTGC CTCCCAGAAC CCCAGCCCAG AACTCTTCAG   676

AGATTTAAGA ATCTCCTCCT ACCTCCTGAC TCAGCNCCAT GTAATCATTA AACTC        731

(2) INFORMATION FOR SEQ ID NO: 2:

(i) SEQUENCE CHARACTERISTICS:
        (A) LENGTH: 127 amino acids
        (B) TYPE: amino acid
        (D) TOPOLOGY: linear (ii) MOLECULE TYPE: protein (xi) SEQUENCE DESCRIPTION: SEQ ID NO: 2:

Met Gln Gln Arg Gly Leu Ala Ile Val Ala Leu Ala Val Cys Ala Ala
-22         -20                 -15                 -10

Leu His Ala Ser Glu Ala Ile Leu Pro Ile Ala Ser Ser Cys Cys Thr
         -5                   1                   5                  10

Glu Val Ser His His Ile Ser Arg Arg Leu Leu Glu Arg Val Asn Met
                 15                  20                  25

Cys Arg Ile Gln Arg Ala Asp Gly Asp Cys Asp Leu Ala Ala Val Ile
             30                  35                  40

Leu His Val Lys Arg Arg Arg Ile Cys Val Ser Pro His Asn His Thr
         45                  50                  55

Val Lys Gln Trp Met Lys Val Gln Ala Ala Lys Lys Asn Gly Lys Gly
     60                  65                  70

Asn Val Cys His Arg Lys Lys His His Gly Lys Arg Asn Ser Asn Arg
 75                  80                  85                  90

Ala His Gln Gly Lys His Glu Thr Tyr Gly His Lys Thr Pro Tyr
                 95                 100                 105

(2) INFORMATION FOR SEQ ID NO: 3:

(i) SEQUENCE CHARACTERISTICS:
        (A) LENGTH: 496 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 3:
```

-continued

```
TCCTGATCGA ACAGCCTCAC TTGTNTTGCT GTCAGTGCCA GTAGGGCAGG CAGGAATGCA        60

GCAGAGAGGA CTCGCCATCG TGGCCTTGGN TGTCTGTGCG GCCCTACATG CCTCAAAAGC       120

CATACTTCCC ATTGCCTCCA GCTGTTGCAC GGAGGTTTCA CATCATATTT CCAGAAGGCT       180

CCTGGGAAAG AGTGAATATG TGTCGCATCC AGAGAGCTGA TGGGGATTGT NACTTGGCTG       240

CTGTCATCCT TCATGTCAAG CGCAGAAGAA TCTGTNTCAG CCCGNACAAC CATACTGTTA       300

AGCAGTGGNT GAAAGTGCAA GTTGCCAGGA AAAATGGTAA AGGAAATTTT TTCCACAGGG       360

NGGAAACACC CTGGGNAAGG GGANCCGTTA CCAGGGNACT TNNGGGGAAA NGGGAAANTT       420

NGGGCNTNAA AAATCCCTTT TNNGGGGNTT TAAGGTAAAT TTTNNNGGGA AATTTTCCNA       480

GGGGNTTTGG NCATTT                                                       496
```

(2) INFORMATION FOR SEQ ID NO: 4:

(i) SEQUENCE CHARACTERISTICS:
        (A) LENGTH: 445 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 4:

```
GGCACGAGCT TTGGCAGCTT CTTCACGTCG GTCCTCTCCG CGCGCGGTAG GAACCGTCCA        60

CGGCCTTAAA GAAGCCTCCT CACCAGCCAT ACTTCCCATT GCCTCCAGCT GTTGCACGGA       120

GGTTTCACAT CATATTTCCA GAAGGCTCCT GGNAAAGAGT GAATATGTGT CGCATCCAGA       180

GAGCTGATGG GGATTGTGAC TTGGCTGCTG TCATCCTTCA TGTCAAGCGC AGAAGAATCT       240

GTGTTCAGCC CGCACAACCA TACTGTTGAA GCAGTGGATG AAAGTGCAAG CTGCCAAGAA       300

AAATGGTAAA GGAAATGTTT GCCACAGGAA GAAACACCNG GCAAGAGGAA CATTAACAGG       360

NACTTCCAGG GGAAACACGA AACTNACGGG CCNGAAAAAT CCTTATTTAG AGATTNACCG       420

TTAANCTACC GGGACATTCC CCAAT                                             445
```

(2) INFORMATION FOR SEQ ID NO: 5:

(i) SEQUENCE CHARACTERISTICS:
        (A) LENGTH: 362 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..336

(ix) FEATURE:
        (A) NAME/KEY: mat_peptide
        (B) LOCATION: 73..336

(xi) SEQUENCE DESCRIPTION: SEQ ID NO: 5:

```
ATG AAG GGG CCC CCA ACC TTC TGC AGC CTC CTG CTG CTG TCA TTG CTC         48
Met Lys Gly Pro Pro Thr Phe Cys Ser Leu Leu Leu Leu Ser Leu Leu
-24             -20                 -15                 -10

CTG AGC CCA GAC CCT ACA GCA GCA TTC CTA CTG CCA CCC AGC ACT GCC         96
Leu Ser Pro Asp Pro Thr Ala Ala Phe Leu Leu Pro Pro Ser Thr Ala
         -5                  1                   5

TGC TGT ACT CAG CTC TAC CGA AAG CCA CTC TCA GAC AAG CTA CTG AGG        144
Cys Cys Thr Gln Leu Tyr Arg Lys Pro Leu Ser Asp Lys Leu Leu Arg
```

```
            10                  15                  20
AAG GTC ATC CAG GTG GAA CTG CAG GAG GCT GAC GGG GAC TGT CAC CTC      192
Lys Val Ile Gln Val Glu Leu Gln Glu Ala Asp Gly Asp Cys His Leu
 25                  30                  35                  40

CAG GCT TTC GTG CTT CAC CTG GCT CAA CGC AGC ATC TGC ATC CAC CCC      240
Gln Ala Phe Val Leu His Leu Ala Gln Arg Ser Ile Cys Ile His Pro
                 45                  50                  55

CAG AAC CCC AGC CTG TCA CAG TGG TTT GAG CAC CAA GAG AGA AAG CTC      288
Gln Asn Pro Ser Leu Ser Gln Trp Phe Glu His Gln Glu Arg Lys Leu
             60                  65                  70

CAT GGG ACT CTG CCC AAG CTG AAT TTT GGG ATG CTA AGG AAA ATG GGC      336
His Gly Thr Leu Pro Lys Leu Asn Phe Gly Met Leu Arg Lys Met Gly
         75                  80                  85

TGAAGCCCCA ATAGCCAAAT AATAAA                                         362

(2) INFORMATION FOR SEQ ID NO: 6:

(i) SEQUENCE CHARACTERISTICS:
        (A) LENGTH: 112 amino acids
        (B) TYPE: amino acid
        (D) TOPOLOGY: linear (ii) MOLECULE TYPE: protein (xi) SEQUENCE DESCRIPTION: SEQ ID NO: 6:

Met Lys Gly Pro Pro Thr Phe Cys Ser Leu Leu Leu Ser Leu Leu
-24                 -20                 -15                 -10

Leu Ser Pro Asp Pro Thr Ala Ala Phe Leu Leu Pro Pro Ser Thr Ala
                 -5                   1                   5

Cys Cys Thr Gln Leu Tyr Arg Lys Pro Leu Ser Asp Lys Leu Leu Arg
         10                  15                  20

Lys Val Ile Gln Val Glu Leu Gln Glu Ala Asp Gly Asp Cys His Leu
 25                  30                  35                  40

Gln Ala Phe Val Leu His Leu Ala Gln Arg Ser Ile Cys Ile His Pro
                 45                  50                  55

Gln Asn Pro Ser Leu Ser Gln Trp Phe Glu His Gln Glu Arg Lys Leu
             60                  65                  70

His Gly Thr Leu Pro Lys Leu Asn Phe Gly Met Leu Arg Lys Met Gly
         75                  80                  85

(2) INFORMATION FOR SEQ ID NO: 7:

(i) SEQUENCE CHARACTERISTICS:
        (A) LENGTH: 433 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 23..382

(ix) FEATURE:
        (A) NAME/KEY: mat_peptide
        (B) LOCATION: 98..382

(xi) SEQUENCE DESCRIPTION: SEQ ID NO: 7:

GAAACCTCTA GGCTGAGTGA GC ATG ATG GAG GGG CTC TCC CCC GCC AGC AGC     52
                        Met Met Glu Gly Leu Ser Pro Ala Ser Ser
                        -25                 -20

CTC CCG CTG TTA CTG TTG CTT CTG AGC CCG GCT CCT GAA GCA GCC TTG     100
```

```
Leu Pro Leu Leu Leu Leu Leu Ser Pro Ala Pro Glu Ala Ala Leu
-15              -10              -5                        1

CCT CTG CCC TCC AGC ACT AGC TGC TGT ACT CAG CTC TAT AGA CAG CCA         148
Pro Leu Pro Ser Ser Thr Ser Cys Cys Thr Gln Leu Tyr Arg Gln Pro
            5                   10                  15

CTC CCA AGC AGG CTG CTG AGG AGG ATT GTC CAC ATG GAA CTG CAG GAG         196
Leu Pro Ser Arg Leu Leu Arg Arg Ile Val His Met Glu Leu Gln Glu
        20                  25                  30

GCC GAT GGG GAC TGT CAC CTC CAG GCT GTC GTG CTT CAC CTG GCT CGG         244
Ala Asp Gly Asp Cys His Leu Gln Ala Val Val Leu His Leu Ala Arg
    35                  40                  45

CGC AGT GTC TGT GTT CAT CCC CAG AAC CGC AGC CTG GCT CGG TGG TTA         292
Arg Ser Val Cys Val His Pro Gln Asn Arg Ser Leu Ala Arg Trp Leu
50                  55                  60                  65

GAA CGC CAA GGG AAA AGG CTC CAA GGG ACT GTA CCC AGT TTA AAT CTG         340
Glu Arg Gln Gly Lys Arg Leu Gln Gly Thr Val Pro Ser Leu Asn Leu
                70                  75                  80

GTA CTA CAA AAG AAA ATG TAC TCA AAC CCC CAA CAG CAA AAC                 382
Val Leu Gln Lys Lys Met Tyr Ser Asn Pro Gln Gln Gln Asn
            85                  90                  95

TAATAAAGCA ACATTAGACG ACAAAAAAAA AAAAAAAAA AAAAAAAAA A                  433

(2) INFORMATION FOR SEQ ID NO: 8:

(i) SEQUENCE CHARACTERISTICS:
        (A) LENGTH: 120 amino acids
        (B) TYPE: amino acid
        (D) TOPOLOGY: linear (ii) MOLECULE TYPE: protein (xi) SEQUENCE DESCRIPTION: SEQ ID NO: 8:

Met Met Glu Gly Leu Ser Pro Ala Ser Ser Leu Pro Leu Leu Leu
-25                  -20                  -15                 -10

Leu Leu Ser Pro Ala Pro Glu Ala Ala Leu Pro Leu Pro Ser Ser Thr
                -5                       1                5

Ser Cys Cys Thr Gln Leu Tyr Arg Gln Pro Leu Pro Ser Arg Leu Leu
        10                  15                  20

Arg Arg Ile Val His Met Glu Leu Gln Glu Ala Asp Gly Asp Cys His
        25                  30                  35

Leu Gln Ala Val Val Leu His Leu Ala Arg Arg Ser Val Cys Val His
40                  45                  50                  55

Pro Gln Asn Arg Ser Leu Ala Arg Trp Leu Glu Arg Gln Gly Lys Arg
                60                  65                  70

Leu Gln Gly Thr Val Pro Ser Leu Asn Leu Val Leu Gln Lys Lys Met
            75                  80                  85

Tyr Ser Asn Pro Gln Gln Gln Asn
            90              95

(2) INFORMATION FOR SEQ ID NO: 9:

(i) SEQUENCE CHARACTERISTICS:
        (A) LENGTH: 99 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO: 9:

Met Lys Val Ser Ala Ala Leu Leu Cys Leu Leu Leu Ile Ala Ala Thr
```

```
                1               5                      10                     15
         Phe Ile Pro Gln Gly Leu Ala Gln Pro Asp Ala Ile Asn Ala Pro Val
                                  20                 25                 30

Thr Cys Cys Tyr Asn Phe Thr Asn Arg Lys Ile Ser Val Gln Arg Leu
                      35                 40                 45

Ala Ser Tyr Arg Arg Ile Thr Ser Ser Lys Cys Pro Lys Glu Ala Val
                 50                 55                 60

Ile Phe Lys Thr Ile Val Ala Lys Glu Ile Cys Ala Asp Pro Lys Gln
         65                  70                 75                     80

Lys Trp Val Gln Asp Ser Met Asp His Leu Asp Lys Gln Thr Gln Thr
                         85                 90                  95

Pro Lys Thr (2) INFORMATION FOR SEQ ID NO: 10:

(i) SEQUENCE CHARACTERISTICS:
              (A) LENGTH: 96 amino acids
              (B) TYPE: amino acid
              (C) STRANDEDNESS: Not Relevant
              (D) TOPOLOGY: linear (ii) MOLECULE TYPE: peptide (xi) SEQUENCE DESCRIPTION: SEQ ID NO: 10:

Met Cys Cys Thr Lys Ser Leu Leu Leu Ala Ala Leu Met Ser Val Leu
    1               5                  10                  15

Leu Leu His Leu Cys Gly Glu Ser Glu Ala Ala Ser Asn Phe Asp Cys
                    20                 25                  30

Cys Leu Gly Tyr Thr Asp Arg Ile Leu His Pro Lys Phe Ile Val Gly
                35                 40                  45

Phe Thr Arg Gln Leu Ala Asn Glu Gly Cys Asp Ile Asn Ala Ile Ile
            50                 55                 60

Phe His Thr Lys Lys Lys Leu Ser Val Cys Ala Asn Pro Lys Gln Thr
    65                  70                 75                      80

Trp Val Lys Tyr Ile Val Arg Leu Leu Ser Lys Lys Val Lys Asp Met
                    85                 90                  95

(2) INFORMATION FOR SEQ ID NO: 11:

(i) SEQUENCE CHARACTERISTICS:
              (A) LENGTH: 543 base pairs
              (B) TYPE: nucleic acid
              (C) STRANDEDNESS: single
              (D) TOPOLOGY: linear (ii) MOLECULE TYPE: cDNA (ix) FEATURE:
              (A) NAME/KEY: CDS
              (B) LOCATION: 1..492

(xi) SEQUENCE DESCRIPTION: SEQ ID NO: 11:

ATG TCG CGA TTG AGG AGA TAC GAG GTG GCG CTG GAA GCG GAG GAG GAG       48
    Met Ser Arg Leu Arg Arg Tyr Glu Val Ala Leu Glu Ala Glu Glu Glu
    1               5                  10                  15

ATC TAC TGG GGC TGC TTC TAC TTT TTT CCT TGG CTG CGA ATG TGG CGC       96
    Ile Tyr Trp Gly Cys Phe Tyr Phe Phe Pro Trp Leu Arg Met Trp Arg
                    20                 25                  30

AGG GAG CGG AGT CCG ATG TCT CCA ACA AGC CAG AGA CTA AGT CTG GAA      144
    Arg Glu Arg Ser Pro Met Ser Pro Thr Ser Gln Arg Leu Ser Leu Glu
                35                 40                 45
```

-continued

```
GCC CCC AGC CTC CCA CTG AGA AGC TGG CAT CCG TGG AAC AAG ACT AAG        192
Ala Pro Ser Leu Pro Leu Arg Ser Trp His Pro Trp Asn Lys Thr Lys
 50                  55                  60

CAG AAG CAA GAA GCC TTG CCT CTG CCC TCC AGC ACT AGC TGC TGT ACT        240
Gln Lys Gln Glu Ala Leu Pro Leu Pro Ser Ser Thr Ser Cys Cys Thr
 65                  70                  75                  80

CAG CTC TAT AGA CAG CCA CTC CCA AGC AGG CTG CTG AGG AGG ATT GTC        288
Gln Leu Tyr Arg Gln Pro Leu Pro Ser Arg Leu Leu Arg Arg Ile Val
                 85                  90                  95

CAC ATG GAA CTG CAG GAG GCC GAT GGG GAC TGT CAC CTC CAG GCT GTC        336
His Met Glu Leu Gln Glu Ala Asp Gly Asp Cys His Leu Gln Ala Val
            100                 105                 110

GTG CTT CAC CTG GCT CGG CGC AGT GTC TGT GTT CAT CCC CAG AAC CGC        384
Val Leu His Leu Ala Arg Arg Ser Val Cys Val His Pro Gln Asn Arg
        115                 120                 125

AGC CTG GCT CGG TGG TTA GAA CGC CAA GGG AAA AGG CTC CAA GGG ACT        432
Ser Leu Ala Arg Trp Leu Glu Arg Gln Gly Lys Arg Leu Gln Gly Thr
    130                 135                 140

GTA CCC AGT TTA AAT CTG GTA CTA CAA AAG AAA ATG TAC TCA AAC CCC        480
Val Pro Ser Leu Asn Leu Val Leu Gln Lys Lys Met Tyr Ser Asn Pro
145                 150                 155                 160

CAA CAG CAA AAC TAATAAAGCA ACATTAGACG ACAAAAAAAA AAAAAAAAA             532
Gln Gln Gln Asn
AAAAAAAAAA A                                                           543
```

(2) INFORMATION FOR SEQ ID NO: 12:

(i) SEQUENCE CHARACTERISTICS:
        (A) LENGTH: 164 amino acids
        (B) TYPE: amino acid
        (D) TOPOLOGY: linear (ii) MOLECULE TYPE: protein (xi) SEQUENCE DESCRIPTION: SEQ ID NO: 12:

```
Met Ser Arg Leu Arg Arg Tyr Glu Val Ala Leu Glu Ala Glu Glu Glu
 1               5                  10                  15

Ile Tyr Trp Gly Cys Phe Tyr Phe Phe Pro Trp Leu Arg Met Trp Arg
                20                  25                  30

Arg Glu Arg Ser Pro Met Ser Pro Thr Ser Gln Arg Leu Ser Leu Glu
            35                  40                  45

Ala Pro Ser Leu Pro Leu Arg Ser Trp His Pro Trp Asn Lys Thr Lys
 50                  55                  60

Gln Lys Gln Glu Ala Leu Pro Leu Pro Ser Ser Thr Ser Cys Cys Thr
 65                  70                  75                  80

Gln Leu Tyr Arg Gln Pro Leu Pro Ser Arg Leu Leu Arg Arg Ile Val
                 85                  90                  95

His Met Glu Leu Gln Glu Ala Asp Gly Asp Cys His Leu Gln Ala Val
            100                 105                 110

Val Leu His Leu Ala Arg Arg Ser Val Cys Val His Pro Gln Asn Arg
        115                 120                 125

Ser Leu Ala Arg Trp Leu Glu Arg Gln Gly Lys Arg Leu Gln Gly Thr
    130                 135                 140

Val Pro Ser Leu Asn Leu Val Leu Gln Lys Lys Met Tyr Ser Asn Pro
145                 150                 155                 160

Gln Gln Gln Asn
```

CCL27 POLYPEPTIDES

This filing is a Continuation-in-Part of U.S. Ser. No. 08/978,964, filed Nov. 26, 1997, now abondoned which claims benefit of U.S. provisional patent applications 60/031,805, filed Nov. 27, 1996; and 60/032,606, filed Dec. 5,1996; and 60/063,259, filed on Oct. 24, 1997; each of which is incorporated herein by reference.

FIELD OF THE INVENTION

The present invention contemplates compositions related to proteins which function in controlling development, differentiation, trafficking, and physiology of mammalian cells, e.g., cells of a mammalian immune system. In particular, it provides proteins which regulate or evidence development, differentiation, and function of various cell types, including hematopoietic cells.

BACKGROUND OF THE INVENTION

The circulating component of the mammalian circulatory system comprises various cell types, including red and white blood cells of the erythroid and myeloid cell lineages. See, e.g., Rapaport (1987) *Introduction to Hematology* (2d ed.) Lippincott, Philadelphia, Pa.; Jandl (1987) *Blood: Textbook of Hematology*, Little, Brown and Co., Boston, Mass.; and Paul (ed.) (1993) *Fundamental Immunology* (3d ed.) Raven Press, N.Y.

For some time, it has been known that the mammalian immune response is based on a series of complex cellular interactions, called the "immune network." Recent research has provided new insights into the inner workings of this network. While it remains clear that much of the response does, in fact, revolve around the network-like interactions of lymphocytes, macrophages, granulocytes, and other cells, immunologists now generally hold the opinion that soluble proteins, known as lymphokines, cytokines, or monokines, play a critical role in controlling these cellular interactions. Thus, there is considerable interest in the isolation, characterization, and mechanisms of action of cell modulatory factors, an understanding of which should lead to significant advancements in the diagnosis and therapy of numerous medical abnormalities, e.g., immune system and other disorders.

Lymphokines apparently mediate cellular activities in a variety of ways. They have been shown to support the proliferation, growth, and differentiation of the pluripotential hematopoietic stem cells into vast numbers of progenitors comprising diverse cellular lineages making up a complex immune system. These interactions between the cellular components are necessary for a healthy immune response. These different cellular lineages often respond in a different manner when lymphokines are administered in conjunction with other agents.

The chemokines are a large and diverse superfamily of proteins. The superfamily is subdivided into two classical branches, based upon whether the first two cysteines in the chemokine motif are adjacent (termed the "C—C" branch), or spaced by an intervening residue ("C-X-C"). A more recently identified branch of chemokines lacks two cysteines in the corresponding motif, and is represented by the chemokines known as lymphotactins. Another recently identified branch has three intervening residues between the two cysteines, e.g., CX3C chemokines. See, e.g., Schall and Bacon (1994) *Current Opinion in Immunology* 6:865–873; and Bacon and Schall (1996) *Int. Arch. Allergy & Immunol.* 109:97–109.

Many factors have been identified which influence the differentiation process of precursor cells, or regulate the physiology or migration properties of specific cell types. These observations indicate that other factors exist whose functions in immune function were heretofore unrecognized. These factors provide for biological activities whose spectra of effects may be distinct from known differentiation or activation factors. The absence of knowledge about the structural, biological, and physiological properties of the regulatory factors which regulate cell physiology in vivo prevents the modulation of the effects of such factors. Thus, medical conditions where regulation of the development or physiology of relevant cells is required remains unmanageable.

BRIEF DESCRIPTION OF THE DRAWING

FIG. 1 shows the alignment of protein sequences: Human MCP-1 (SEQ ID NO: 9) is GenBank Accession number S71513; human MIP-3α (SEQ ID NO: 10) is GenBank Accession number U77035.

SUMMARY OF THE INVENTION

The present invention reveals the existence of previously unknown chemokine-motif containing molecules which are hereby designated CCL28 (previously known as: DVic-1; MEC; and PLACC) and CCL27 (previously known as CTACK; DGWCC; Eskine; ILC; and ALP). Based on sequence analysis of the chemokine protein sequences described below, it is apparent that the CCL27 and CCL28 belong to the CC chemokine family. The present invention provides an isolated or purified polynucleotide encoding a polypeptide comprising the amino acid sequence of SEQ ID NO: 2 or SEQ ID NO: 6, or an antigenic fragment thereof. Also provided is an isolated and purified polynucleotide having a sequence which is complementary to the polynucleotide of SEQ ID NO: 2 or SEQ ID NO: 6. In another embodiment, the polynucleotide can be detectably labeled.

The present invention further provides a method of detection comprising: a) hybridizing the polynucleotide of claim 3 to a sample containing nucleic acids under conditions suitable for the formation of a hybridization complex; and b) detecting the hybridization complex. In another embodiment, the polynucleotide is amplified prior to hybridization.

The present invention encompasses an isolated or purified polynucleotide which hybridizes under stringent conditions to the polynucleotide of SEQ ID NO:2 or SEQ ID NO:6. Also encompassed is an expression vector comprising the polynucleotide SEQ ID NO: 2 or SEQ ID NO: 6, and a host cell comprising the expression vector.

Also encompassed is a method of producing a polypeptide comprising: a) culturing the host cell of claim 8 under conditions suitable for the expression of the polypeptide; and b) recovering the polypeptide form the host cell culture.

The present invention provides a substantially purified polypeptide comprising the amino acid sequence of SEQ ID NO:2 or SEQ ID NO:6 or an antigenic fragment thereof. In another embodiment the polypeptide has 80% amino acid sequence identity to SEQ ID NO: 2 or SEQ ID NO: 6. In another embodiment the polypeptide has 90% identity to SEQ ID NO: 2 or SEQ ID NO: 6. Also encompassed is a pharmaceutical composition comprising the polypeptide of SEQ ID NO: 2 or SEQ ID NO: 6 in conjunction with a suitable carrier.

The present invention provides a substantially purified binding composition which binds to the polypeptide of SEQ ID NO: 2 or SEQ ID NO: 6. In another embodiment the binding composition is an antibody. The antibody can be: a) a polyclonal antibody; b) a monoclonal antibody; c) a single chain antibody; d) an Fab fragment; e) an Fv fragment; or f) a humanized antibody. In another embodiment the antibody is 6 capable of blocking the binding of SEQ ID NO: 2 or SEQ ID NO: 6 to a receptor. Also encompassed is a pharmaceutical composition comprising the antibody in conjunction with a suitable carrier.

The present invention provides a method of modulating physiology or development of a cell or tissue culture cells comprising exposing said cell to an agonist or antagonist of SEQ ID NO: 2 or SEQ ID NO: 6. In a further embodiment the antagonist is an antibody.

DETAILED DESCRIPTION

I. General

The present invention provides primate DNA sequences encoding proteins which exhibit structural properties or motifs characteristic of a cytokine or chemokine. For a review of the chemokine family, see, e.g., Lodi, et al. (1994) *Science* 263:1762–1767; Gronenborn and Clore (1991) *Protein Engineering* 4:263–269; Miller and Kranger (1992) *Proc. Nat'l Acad. Sci. USA* 89:2950–2954; Matsushima and Oppenheim (1989) *Cytokine* 1:2–13; Stoeckle and Baker (1990) *New Biol.* 2:313–323; Oppenheim, et al. (1991) *Ann. Rev. Immunol.* 9:617–648; Schall (1991) *Cytokine* 3:165–183; and *The Cytokine Handbook* Academic Press, NY.

The new cytokines described herein are designated CCL28 and CCL27. See the Sequence Listing. The descriptions below are directed, for exemplary purposes, to primate embodiments, e.g., human, but are likewise applicable to related embodiments from other, e.g., natural, mammalian sources, including rodent. These sources should include various vertebrates, typically warm blooded animals, e.g., birds and mammals, particularly domestic animals, rodents, and primates. Comparison to other chemokines is provided in FIG. 1.

The chemokine proteins of this invention are defined in part by their physicochemical and biological properties. The biological properties of the chemokines described herein, e.g., CCL28 or CCL27, are defined, in part, by their amino acid sequence, and mature size. They also should share at least some biological properties with other similar chemokines. One of skill will readily recognize that some sequence variations may be tolerated, e.g., conservative substitutions or positions remote from the critical residues for receptor interaction or important tertiary structure features, without altering significantly the biological activity of the molecule. Conversely, non-conservative substitutions may be adapted to delete selected functions.

These chemokines are present in specific tissue types, e.g., skin tissues, and the interaction of the protein with a receptor will be important for mediating various aspects of cellular physiology or development. The cellular types which express message encoding CCL28 or CCL27 suggest that signals important in cell differentiation and development are mediated by them. See, e.g., Gilbert (1991) *Developmental Biology* (3d ed.) Sinauer Associates, Sunderland, Mass.; Browder, et al. (1991) *Developmental Biology* (3d ed.) Saunders, Philadelphia, Pa.; Russo, et al. (1992) *Development: The Molecular Genetic Approach* Springer-Verlag, New York, N.Y.; and Wilkins (1993) *Genetic Analysis of Animal Development* (2d ed.) Wiley-Liss, New York, N.Y.

Moreover, CCL28 or CCL27 expression or responsiveness should serve as markers, e.g., to define certain cell subpopulations.

The new chemokines were discovered through searches and careful analysis of database sequences. The absence of sequences in available databases strongly suggests that the messages are rarely expressed, and/or at very low levels. Such may reflect highly restricted cell expression and/or very low levels in most cell types.

CCL27 is closely homologous to CCL28, as shown by the alignment of these two cytokines (FIG. 1). The sequences of MCP-1 (SEQ ID NO:9) and MIP-3α (SEQ ID NO:10) are also shown. Human CCL27 (SEQ ID Nos. 5 and 6) and human CCL28 (SEQ ID Nos. 1 and 2) share a 49% nucleotide identity for the coding sequence, and about 40% amino acid identity in the common homology region (Pan, et al. (2000) *J. Immunol.* 165:2943–2949; Wang, et al. (2000) *J. Biol. Chem.* 275:22313–22323). Both CCL27 and CCL28 bind to the same receptor, CCR10, though CCL28 can also bind to another receptor, CCR3 (Pan, et al. (2000) *J. Immunol.* 165:2943–2949).

Human CCL27 (SEQ ID NO:6) and murine CCL27 (SEQ ID NO:8) share a 78% amino acid similarity. The predicted mature human and murine CCL27 polypeptides are 84% similar (Morales, et al. (1999) *Proc. Natl. Acad. Sci. USA* 96:14470–14475). Screening of mouse cDNA libraries also provided a longer transcript (SEQ ID NO:11) and polypeptide (SEQ ID NO:12) of murine CCL28, where the extra amino acids appear to contribute to a longer leader sequence for SEQ ID NO:12.

Human CCL28 (SEQ ID NO:1 and 2) is a CC chemokine of 127 amino acids, with a predicted 22 amino acid N-terminal signal peptide. Murine CCL28 is a CC chemokine of 130 amino acids. Human and mouse CCL28 share a 76% sequence identity in the polynucleotide coding region, and share 83 identical amino acids (Wang, et al. (2000) *J. Biol. Chem.* 275:22313–22323). Initial phases of this work revealed expressed sequence tags (ESTs) derived from human fetal heart (SEQ ID NO:3) and human osteoblast (SEQ ID NO:4) cDNA libraries that contained partial length sequences for the open reading frame of CCL28 (Wang, et al. (2000) supra).

CCL28 and CCL27 have been shown to share a common receptor which has been identified as CCR10 (a.k.a. GPR2; see, e.g., Homey, et al. (2000) *J. Immunol.* 164:3465–3470.). As noted below CCL27 is secreted by keratinocytes and binds to CCR10, which has high expression levels on T cells which express Cutaneous Lymphocyte-associated Antigen (CLA; see, e.g., Homey, et al. (2002) *Nature Med.* 8:157–165). CCL27 attracts CLA+ memory T cells and further, allergen induced skin inflammation (see, e.g., Santamaria, et al. (1995) *Intl. Arch. Allergy Immunol.* 107: 359–362) was ameliorated with administration of anti-CCL27 antibodies. Therefore agonists of the present invention are useful in the treatment of infectious disorders, in particular, infections of the skin. Antagonists of the present invention are useful for the treatment of inflammatory disorders, in particular, skin inflammatory disorders, including, but not limited to, psoraisis, atopic dermatitis, contact dermatitis, etc.

II. Definitions

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, including selenomethionine, as well as those amino acids that are modified after incorporation into a polypeptide, e.g., hydroxyproline, O-phosphoserine, O-phosphotyrosine, γ-carboxyglutamate, and cystine. Amino acid analogs refers to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. Amino acids may be referred to herein by either their commonly known three letter symbols or by their one-letter symbols.

The term "binding composition" refers to molecules that bind with specificity and selectivity to a CCL28 or CCL27 chemokine, e.g., in an antibody-antigen interaction. However, other compounds, e.g., receptor proteins, may also specifically and/or selectively associate with CCL28 or CCL27 chemokines to the exclusion of other molecules. Typically, the association will be in a natural physiologically relevant protein-protein interaction, either covalent or non-covalent, and may include members of a multiprotein complex, including carrier compounds or dimerization partners. The molecule may be a polymer, or chemical reagent. No implication as to whether a CCL28 or CCL27 chemokine is necessarily a convex shaped molecule, e.g., the ligand or the receptor of a ligand-receptor interaction, is necessarily represented, other than whether the interaction exhibits similar specificity, e.g., specific affinity. A functional analog may be a ligand with structural modifications, or may be a wholly unrelated molecule, e.g., which has a molecular shape which interacts with the appropriate ligand binding determinants. The ligands may serve as agonists or antagonists of the receptor, see, e.g., Goodman, et al. (eds.) (1990) *Goodman & Gilman's: The Pharmacological Bases of Therapeutics* (8th ed.) Pergamon Press, Tarrytown, N.Y.

The term "binding agent:chemokine protein complex", as used herein, refers to a complex of a binding agent and a chemokine, e.g., CCL28 or CCL27, protein that is formed by specific binding of the binding agent to the chemokine protein. Specific or selective binding of the binding agent means that the binding agent has a specific binding site, e.g., antigen binding site, that recognizes a site on the CCL28 chemokine protein that is not shared in many other proteins. For example, antibodies raised to a CCL28 chemokine protein and recognizing an epitope on the chemokine protein are capable of forming a binding agent: CCL28 chemokine protein complex by specific and selective binding. Typically, the formation of a binding agent:CCL28 chemokine protein complex allows the measurement of CCL28 chemokine protein in a mixture of other proteins and biologics. Likewise, the term "antibody:CCL27 chemokine protein complex" refers to an embodiment in which the binding agent, e.g., is the antigen binding portion from an antibody. The antibody may be monoclonal, polyclonal, or a binding fragment of an antibody, e.g., an Fab or F(ab)2 fragment. The antibody will preferably be a polyclonal antibody for cross-reactivity testing purposes.

As used herein, the term "biological activity" is used to describe, without limitation, metabolic, signaling, hormonal, developmental, embryological, proliferative, apoptotic, secretory, migratory, adhesive, neurological, pathological, inflammatory, and cancerous activities of a cell, tissue, organ, or animal, a cultured cell or tissue, a perfused tissue or organ, or animal sustained on life support. "Biological activity" also includes the catalytic activity of enzymes in vivo and enzymes in the purified state, as well as changes in conformation in enzymes and other proteins.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a conserved amino acid or a small percentage of amino acids in the encoded sequence is a "conservatively modified variant." Conservative substitution tables providing functionally similar amino acids are well known in the art. An example of a conservative substitution is the exchange of an amino acid in one of the following groups for another amino acid of the same group (see, e.g., U.S. Pat. No. 5,767,063; and Kyte and Doolittle (1982) *J. Mol. Biol.* 157:105–132).

(1) Hydrophobic: Norleucine, Ile, Val, Leu, Phe; Cys; or Met;
(2) Neutral hydrophilic: Cys, Ser, Thr;
(3) Acidic: Asp, Glu;
(4) Basic: Asn, Gln, His, Lys, Arg;
(5) Residues that influence chain orientation: Gly; Pro; and
(6) Aromatic: Trp; Tyr; Phe.
(7) Small amino acids: Gly, Ala, Ser.

A polypeptide "fragment", "antigenic fragment", "immunogenic fragment" or "segment", as used herein, encompasses a a stretch of contiguous amino acid residues of at least about 8 amino acids, generally at least 10 amino acids, more generally at least 12 amino acids, often at least 14 amino acids, more often at least 16 amino acids, typically at least 18 amino acids, more typically at least 20 amino acids, usually at least 22 amino acids, more usually at least 24 amino acids, preferably at least 26 amino acids, more preferably at least 28 amino acids, and, in particularly preferred embodiments, at least about 30 or more amino acids, e.g., 35, 40, 45, 50, 60, 70, 80, 100, 200, etc. The invention further comprises proteins or polypeptides comprising a plurality of said segments, e.g., distinct, non-overlapping, segments of a specified length. Typically, the plurality will be at least two, more usually at least three, and preferably 4, 5, 6, 7, or even more. While the length minima are provided, longer lengths, of various sizes, may be appropriate, e.g., one of length 7, and two of length 12. Those skilled in the are will understand that antigenic or immunogenic fragments will be those use to raise binding composition, specifically antibodies. Features of one of the different polypeptides or proteins defined in such a manner should not be taken to limit those of another of the polypeptides or proteins of the invention.

"Homologous" nucleic acid sequences, when compared, exhibit significant similarity, or identity. The standards for homology in nucleic acids are either measures for homology generally used in the art by sequence comparison and/or phylogenetic relationship, or based upon hybridization conditions. Hybridization conditions are described in greater detail below.

"Humanized antibody" means an antibody comprising an antigen-binding region of nonhuman origin, e.g., rodent, and at least a portion of an immunoglobin of human origin, e.g., a human framework region, a human constant region, or portion thereof (see, e.g., U.S. Pat. No. 6,352,832).

"Immune disorder" is defined as any condition where cells of the immune system, or molecules generally associated with the immune system, e.g., cytokines, chemokines, and receptors thereof, contribute to the suffering of a patient or, in the alternative, are not functioning optimally to maintain the health of a patient. Immune disorders include inflammatory conditions, e.g., psoriasis, allergies, asthma, rheumatoid arthritis, and cancer, metastasis, and the angiogenesis of tumors.

"Nucleic acid" refers to deoxyribonucleotides or ribonucleotides and polymers thereof in either single stranded or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids. An "isolated" nucleic acid is a nucleic acid, e.g., an RNA, DNA, or a mixed polymer, which is substantially separated from other biologic components which naturally accompany a native sequence, e.g., proteins and flanking genomic sequences from the originating species. The term embraces a nucleic acid sequence which has been removed from its naturally occurring environment, and includes recombinant or cloned DNA isolates and chemically synthesized analogs, or analogs biologically synthesized by heterologous systems. A substantially pure molecule includes isolated forms of the molecule. An isolated nucleic acid will usually contain homogeneous nucleic acid molecules, but will, in some embodiments, contain nucleic acids with minor sequence heterogeneity. This heterogeneity is typically found at the polymer ends or portions not critical to a desired biological function or activity.

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., (1991) *Nucleic Acids Res.* 19:5081; Ohtsuka, et al. (1985) *J. Biol. Chem.* 260:2605–2608; Rossolini et al. (1994) *Mol. Cell. Probes* 8:91–98). The term nucleic acid may be used interchangeably with gene, cDNA, mRNA, oligonucleotide, and polynucleotide.

A particular nucleic acid sequence also implicitly encompasses "allelic variants" and "splice variants." Similarly, a particular protein encoded by a nucleic acid implicitly encompasses any protein encoded by an allelic variant and splice variant of that nucleic acid. "Splice variants" are products of alternative splicing of mRNA. After transcription, an mRNA may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. It will be understood that inasmuch as natural allelic variations exist and occur from individual to individual, as demonstrated by (an) amino acid difference(s) in the overall sequence or by deletions, substitutions, insertions, inversions, or additions of one or more amino acids of said sequences, the present invention is intended to embrace all of such allelic variations of the two molecules involved.

The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

As used herein, the term "CCL28 chemokine protein" shall encompass, when used in a protein context, a protein having amino acid sequences, particularly from the chemokine motif portions, shown in SEQ ID NO: 2, or a significant fragment unique to and/or characteristic of such a protein, preferably a natural embodiment. Likewise for the human and mouse CCL27, and SEQ ID NO: 6 and 8. The invention also embraces a polypeptide which exhibits similar structure to such chemokines, e.g., which interacts with CCL28 or CCL27 chemokine specific binding components. These binding components, e.g., antibodies, typically bind to either CCL28 or CCL27 chemokine with high affinity, e.g., at least about 100 nM, usually better than about 30 nM, preferably better than about 10 nM, and more preferably at better than about 3 nM.

The term "polypeptide" or "protein" as used herein includes a significant fragment or segment of chemokine motif portion of, e.g., a CCL27 chemokine, and encompasses a stretch of amino acid residues of at least about 8 amino acids, generally at least 10 amino acids, more generally at least 12 amino acids, often at least 14 amino acids, more often at least 16 amino acids, typically at least 18 amino acids, more typically at least 20 amino acids, usually at least 22 amino acids, more usually at least 24 amino acids, preferably at least 26 amino acids, more preferably at least 28 amino acids, and, in particularly preferred embodiments, at least about 30 or more amino acids, e.g., 35, 40, 45, 50, 60, 70, 80, etc. The segments may have amino and carboxy termini, with appropriate lengths, e.g., starting, e.g., at residue 1, 2, 3, etc., and ending at, e.g., residue 95, 94, 93, 92, etc. The invention encompasses proteins comprising a plurality of said segments.

A "recombinant" nucleic acid is defined either by its method of production or its structure. In reference to its method of production, e.g., a product made by a process, the process is use of recombinant nucleic acid techniques, e.g., involving human intervention in the nucleotide sequence, typically selection or production. Alternatively, it can be a nucleic acid made by generating a sequence comprising fusion of two fragments which are not naturally contiguous to each other, but is meant to exclude products of nature, e.g., naturally occurring mutants. Thus, for example, products made by transforming cells with any non-naturally occurring vector is encompassed, as are nucleic acids comprising sequence derived using any synthetic oligonucleotide process. Such is often done to replace a codon with a redundant codon encoding the same or a conservative amino acid, while typically introducing or removing a sequence recognition site. Alternatively, it is performed to join together nucleic acid segments of desired functions to generate a single genetic entity comprising a desired combination of functions not found in the commonly available natural forms. Restriction enzyme recognition sites are often the target of such artificial manipulations, but other site specific targets, e.g., promoters, DNA replication sites, regulation sequences, control sequences, or other useful features may be incorporated by design. A similar concept is intended for a recombinant, e.g., fusion, polypeptide. Specifically included are synthetic nucleic acids which, by genetic code redundancy, encode polypeptides similar to fragments of these antigens, and fusions of sequences from various different species variants.

"Substantially pure" in a protein context typically means that the protein is isolated from other contaminating proteins, nucleic acids, and other biologicals derived from the original source organism. Purity, or "isolation" may be assayed by standard methods, and will ordinarily be at least about 50% pure, more ordinarily at least about 60% pure, generally at least about 70% pure, more generally at least about 80% pure, often at least about 85% pure, more often at least about 90% pure, preferably at least about 95% pure, more preferably at least about 98% pure, and in most preferred embodiments, at least 99% pure. Similar concepts apply, e.g., to antibodies or nucleic acids.

"Substantial similarity" in the nucleic acid sequence comparison context means either that the segments, or their complementary strands, when compared, are identical when optimally aligned, with appropriate nucleotide insertions or deletions, in at least about 50% of the nucleotides, generally at least 56%, more generally at least 59%, ordinarily at least 62%, more ordinarily at least 65%, often at least 68%, more often at least 71%, typically at least 74%, more typically at least 77%, usually at least 80%, more usually at least about 85%, preferably at least about 90%, more preferably at least about 95 to 98% or more, and in particular embodiments, as high at about 99% or more of the nucleotides. Alternatively, substantial similarity exists when the segments will hybridize under selective hybridization conditions, to a strand, or its complement, typically using a sequence derived from SEQ ID NO: 1, 5, or 7. Typically, selective hybridization will occur when there is at least about 55% similarity over a stretch of at least about 30 nucleotides, preferably at least about 65% over a stretch of at least about 25 nucleotides, more preferably at least about 75%, and most preferably at least about 90% over about 20 nucleotides. See Kanehisa (1984) Nuc. Acids Res. 12:203–213. The length of similarity comparison, as described, may be over longer stretches, and in certain embodiments will be over a stretch of at least about 17 nucleotides, usually at least about 20 nucleotides, more usually at least about 24 nucleotides, typically at least about 28 nucleotides, more typically at least about 40 nucleotides, preferably at least about 50 nucleotides, and more preferably at least about 75 to 100 or more nucleotides, e.g., 150, 200, etc.

Methods of alignment of sequences for comparison are well-known in the art. Optimal alignment of sequences for comparison can be conducted, e.g., by the local homology algorithm of Smith and Waterman (1981) Adv. Appl. Math. 2:482, by the homology alignment algorithm of Needleman and Wunsch (1970) J. Mol. Biol. 48:443, by the search for similarity method of Pearson and Lipman (1988) Proc. Natl. Acad. Sci. USA 85:2444, by computerized implementations of these algorithms, as those provided by software packages, such as MacVector 7.1® from Accelrys, Inc. (San Diego, Calif.) and Vector NTI® Suite from InforMax, Inc. (Bethesda, Md.). See also, e.g., Needleham, et al., (1970) J. Mol. Biol. 48:443–453; Sankoff, et al. (1983) Time Warps, String Edits, and Macromolecules: The Theory and Practice of Sequence Comparison, Addison-Wesley, Reading, Mass.

"Stringent conditions", in referring to homology or substantial similarity in the hybridization context, will be stringent combined conditions of salt, temperature, organic solvents, and other parameters, typically those controlled in hybridization reactions. The combination of parameters is more important than the measure of any single parameter. See, e.g., Wetmur and Davidson (1968) J. Mol. Biol. 31:349–370. A nucleic acid probe which binds to a target nucleic acid under stringent conditions is specific for said target nucleic acid. Such a probe is typically more than 11 nucleotides in length, and is sufficiently identical or complementary to a target nucleic acid over the region specified by the sequence of the probe to bind the target under stringent hybridization conditions.

CCL27 chemokines from other mammalian species can be cloned and isolated by cross-species hybridization of closely related species. See, e.g., below. Similarity may be relatively low between distantly related species, and thus hybridization of relatively closely related species is advisable. Alternatively, preparation of an antibody preparation which exhibits less species specificity may be useful in expression cloning approaches.

The phrase "specifically binds to an antibody" or "specifically immunoreactive with", when referring to a protein or peptide, refers to a binding reaction which is determinative of the presence of the protein in the presence of a heterogeneous population of proteins and other biological components. Thus, under designated immunoassay conditions, the specified antibodies bind to a particular protein and do not significantly bind other proteins present in the sample. Specific binding to an antibody under such conditions may require an antibody that is selected for its specificity for a particular protein. For example, antibodies raised to the CCL28 or CCL27 chemokine protein immunogen with the amino acid sequence depicted in SEQ ID NO: 2, or 6 or 8, can be selected to obtain antibodies specifically immunoreactive with CCL27 chemokine proteins and not with other proteins. The antibodies may be species specific, e.g., also recognizing polymorphic and splicing or developmental variants.

"Therapeutically effective amount" of a therapeutic agent is defined as an amount of each active component of the pharmaceutical formulation that is sufficient to show a meaningful patient benefit, i.e., to cause a decrease in or amelioration of the symptoms of the condition being treated. When the pharmaceutical formulation comprises a diagnostic agent, "a therapeutically effective amount" is defined as an amount of each active component of the pharmaceutical formulation that is sufficient to produce an image or other diagnostic parameter in the diagnostic system employed. When applied to an individual active ingredient, administered alone, the term refers to that ingredient alone. When applied to a combination of active ingredients, the term refers to combined amounts of the active ingredients that result in the therapeutic effect, whether administered in combination, serially or simultaneously. Effective amounts of the pharmaceutical formulation will vary according to factors such as the degree of susceptibility of the individual, the age, sex, and weight of the individual, and idiosyncratic responses of the individual (see, e.g., U.S. Pat. No. 5,888,530).

III. Nucleic Acids

CCL27 chemokine is exemplary of structurally and functionally related proteins. These soluble chemokine proteins will serve to transmit signals between different cell types. The preferred embodiments, as disclosed, will be useful in standard procedures to isolate genes from different individuals or other species, e.g., warm blooded animals, such as birds and mammals. Cross hybridization will allow isolation of related genes encoding proteins from individuals, strains, or species. A number of different approaches are available to successfully isolate a suitable nucleic acid clone based upon the information provided herein. Southern blot hybridization studies can qualitatively determine the presence of homologous genes in human, monkey, rat, mouse, dog, cat, cow, and rabbit genomes under specific hybridization conditions.

Complementary sequences will also be used as probes or primers. Based upon identification of the likely amino terminus, other peptides should be particularly useful, e.g., coupled with anchored vector or poly-A complementary PCR techniques or with complementary DNA of other peptides.

Techniques for nucleic acid manipulation of genes encoding CCL27 chemokine proteins, such as subcloning nucleic acid sequences encoding polypeptides into expression vectors, labeling probes, DNA hybridization, and the like are described generally in Sambrook, et al. (1989) *Molecular Cloning: A Laboratory Manual* (2nd ed.) Vol. 1–3, Cold Spring Harbor Laboratory, Cold Spring Harbor Press, NY, which is incorporated herein by reference. This manual is hereinafter referred to as "Sambrook, et al."

There are various methods of isolating DNA sequences encoding CCL27 chemokine proteins. For example, DNA is isolated from a genomic or cDNA library using labeled oligonucleotide probes having sequences identical or complementary to the sequences disclosed herein. Full-length probes may be used, or oligonucleotide probes may be generated by comparison of the sequences disclosed. Such probes can be used directly in hybridization assays to isolate DNA encoding CCL27 chemokine proteins, or probes can be designed for use in amplification techniques such as PCR, for the isolation of DNA encoding CCL27 chemokine proteins. Reverse translation computer programs can also provide alternative nucleic acid sequences which encode the same proteins.

To prepare a cDNA library, mRNA is isolated from cells which expresses a CCL27 chemokine protein. cDNA is prepared from the mRNA and ligated into a recombinant vector. The vector is transfected into a recombinant host for propagation, screening, and cloning. Methods for making and screening cDNA libraries are well known. See Gubler and Hoffman (1983) *Gene* 25:263–269 and Sambrook, et al.

For a genomic library, the DNA can be extracted from tissue and either mechanically sheared or enzymatically digested to yield fragments of about 12–20 kb. The fragments are then separated by gradient centrifugation and cloned in bacteriophage lambda vectors. These vectors and phage are packaged in vitro, as described in Sambrook, et al. Recombinant phage are analyzed by plaque hybridization as described in Benton and Davis (1977) *Science* 196:180–182. Colony hybridization is carried out as generally described in e.g., Grunstein, et al. (1975) *Proc. Natl. Acad. Sci. USA.* 72:3961–3965.

DNA encoding a CCL27 chemokine protein can be identified in either cDNA or genomic libraries by its ability to hybridize with the nucleic acid probes described herein, e.g., in colony or plaque hybridization assays. The corresponding DNA regions are isolated by standard methods familiar to those of skill in the art. See, e.g., Sambrook, et al.

Various methods of amplifying target sequences, such as the polymerase chain reaction, can also be used to prepare DNA encoding CCL27 chemokine proteins. Polymerase chain reaction (PCR) technology is used to amplify such nucleic acid sequences directly from mRNA, from cDNA, and from genomic libraries or cDNA libraries. The isolated sequences encoding CCL27 chemokine proteins may also be used as templates for PCR amplification.

Typically, in PCR techniques, oligonucleotide primers complementary to two 5' regions in the DNA region to be amplified are synthesized. The polymerase chain reaction is then carried out using the two primers. See Innis, et al. (eds.) (1990) *PCR Protocols: A Guide to Methods and Applications* Academic Press, San Diego, Calif. Primers can be selected to amplify the entire regions encoding a full-length CCL27 chemokine protein or to amplify smaller DNA segments as desired. Once such regions are PCR-amplified, they can be sequenced and oligonucleotide probes can be prepared from sequence obtained using standard techniques. These probes can then be used to isolate DNA's encoding CCL27 chemokine proteins.

Oligonucleotides for use as probes are usually chemically synthesized according to the solid phase phosphoramidite triester method first described by Beaucage and Carruthers (1983) *Tetrahedron Lett.* 22(20):1859–1862, or using an automated synthesizer, as described in Needham-VanDevanter, et al. (1984) *Nucleic Acids Res.* 12:6159–6168. Purification of oligonucleotides is performed e.g., by native acrylamide gel electrophoresis or by anion-exchange HPLC as described in Pearson and Regnier (1983) *J. Chrom.* 255:137–149. The sequence of the synthetic oligonucleotide can be verified using, e.g., the chemical degradation method of Maxam and Gilbert in Grossman and Moldave (eds. 1980) *Methods in Enzymology* 65:499–560 Academic Press, New York.

An isolated nucleic acid encoding a CCL27 chemokine protein was identified. The nucleotide sequence and corresponding open reading frame are provided in SEQ ID NO: 1 or 5 or 7

These CCL27 and CCL28 chemokines exhibit limited similarity to portions of chemokines. See, e.g., Matsushima and Oppenheim (1989) *Cytokine* 1:2–13; Oppenheim, et al. (1991) *Ann. Rev. Immunol.* 9:617–648; Schall (1991) *Cytokine* 3:165–183; and Gronenborn and Clore (1991) *Protein Engineering* 4:263–269. Other features of comparison are apparent between the CCL27 chemokine and chemokine families. See, e.g., Lodi, et al. (1994) *Science* 263:1762–1766. In particular, β-sheet and α-helix residues can be determined using, e.g., RASMOL program, see Sayle and Milner-White (1995) *TIBS* 20:374–376; or Gronenberg, et al. (1991) *Protein Engineering* 4:263–269; and other structural features are defined in Lodi, et al. (1994) *Science* 263:1762–1767. These secondary and tertiary features assist in defining further the C, CC, CXC, and CX3C structural features, along with spacing of appropriate cysteine residues.

This invention provides isolated DNA or fragments to encode a CCL28 or CCL27 chemokine protein. In addition, this invention provides isolated or recombinant DNA which encodes a protein or polypeptide which is capable of hybridizing under appropriate conditions, e.g., high stringency, with the DNA sequences described herein. Said biologically active protein or polypeptide can be an intact ligand, or fragment, and have an amino acid sequence as disclosed in SEQ ID NO: 2 or 6 or 8, particularly natural embodiments. Preferred embodiments will be full length natural sequences, from isolates, e.g., about 11,000 to 12,500 daltons in size when unglycosylated, or fragments of at least about 6,000 daltons, more preferably at least about 8,000 daltons. In glycosylated form, the protein may exceed 12,500 daltons. Further, this invention contemplates the use of isolated or recombinant DNA, or fragments thereof, which encode proteins which are homologous to a CCL28 or CCL27 chemokine protein or which were isolated using cDNA encoding a CCL28 or CCL27 chemokine protein as a probe. The isolated DNA can have the respective regulatory sequences in the 5' and 3' flanks, e.g., promoters, enhancers, poly-A addition signals, and others. Also embraced are methods for making expression vectors with these sequences, or for making, e.g., expressing and purifying, protein products.

IV. Making CCL28, CCL27 Chemokines

DNAs which encode a CCL28 or CCL27 chemokine or fragments thereof can be obtained by chemical synthesis, screening cDNA libraries, or by screening genomic libraries prepared from a wide variety of cell lines or tissue samples. Methods for doing so, or making expression vectors are described herein.

These DNAs can be expressed in a wide variety of host cells for the synthesis of a full-length protein or fragments which can in turn, e.g., be used to generate polyclonal or monoclonal antibodies; for binding studies; for construction and expression of modified molecules; and for structure/function studies. Each CCL28 or CCL27 chemokine or its fragments can be expressed in host cells that are transformed or transfected with appropriate expression vectors. These molecules can be substantially purified to be free of protein or cellular contaminants, other than those derived from the recombinant host, and therefore are particularly useful in pharmaceutical compositions when combined with a pharmaceutically acceptable carrier and/or diluent. The antigen, e.g., CCL27 chemokine, or portions thereof, may be expressed as fusions with other proteins or possessing an epitope tag.

Expression vectors are typically self-replicating DNA or RNA constructs containing the desired antigen gene or its fragments, usually operably linked to appropriate genetic control elements that are recognized in a suitable host cell. The specific type of control elements necessary to effect expression will depend upon the eventual host cell used. Generally, the genetic control elements can include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and sequences that terminate transcription and translation. Expression vectors also usually contain an origin of replication that allows the vector to replicate independently from the host cell.

The vectors of this invention contain DNAs which encode a CCL28 or CCL27 chemokine, or a fragment thereof, typically encoding, e.g., a biologically active polypeptide, or protein. The DNA can be under the control of a viral promoter and can encode a selection marker. This invention further contemplates use of such expression vectors which are capable of expressing eukaryotic cDNA coding for a CCL28 or CCL27 chemokine protein in a prokaryotic or eukaryotic host, where the vector is compatible with the host and where the eukaryotic cDNA coding for the protein is inserted into the vector such that growth of the host containing the vector expresses the cDNA in question. Usually, expression vectors are designed for stable replication in their host cells or for amplification to greatly increase the total number of copies of the desirable gene per cell. It is not always necessary to require that an expression vector replicate in a host cell, e.g., it is possible to effect transient expression of the protein or its fragments in various hosts using vectors that do not contain a replication origin that is recognized by the host cell. It is also possible to use vectors that cause integration of a CCL28 or CCL27 chemokine gene or its fragments into the host DNA by recombination, or to integrate a promoter which controls expression of an endogenous gene.

Vectors, as used herein, contemplate plasmids, viruses, bacteriophage, integratable DNA fragments, and other vehicles which enable the integration of DNA fragments into the genome of the host. Expression vectors are specialized vectors which contain genetic control elements that effect expression of operably linked genes. Plasmids are the most commonly used form of vector, but many other forms of vectors which serve an equivalent function are suitable for use herein. See, e.g., Pouwels, et al. (1985 and Supplements) *Cloning Vectors: A Laboratory Manual* Elsevier, N.Y.; and Rodriquez, et al. (eds.) (1988) *Vectors: A Survey of Molecular Cloning Vectors and Their Uses* Buttersworth, Boston, Mass.

Suitable host cells include prokaryotes, lower eukaryotes, and higher eukaryotes. Prokaryotes include both gram negative and gram positive organisms, e.g., *E. coli* and *B. subtilis*. Lower eukaryotes include yeasts, e.g., *S. cerevisiae* and *Pichia*, and species of the genus *Dictyostelium*. Higher eukaryotes include established tissue culture cell lines from animal cells, both of non-mammalian origin, e.g., insect cells, and birds, and of mammalian origin, e.g., human, primates, and rodents.

Prokaryotic host-vector systems include a wide variety of vectors for many different species. As used herein, *E. coli* and its vectors will be used generically to include equivalent vectors used in other prokaryotes. A representative vector for amplifying DNA is pBR322 or its derivatives. Vectors that can be used to express CCL27 chemokines or CCL27 chemokine fragments include, but are not limited to, such vectors as those containing the lac promoter (pUC-series); trp promoter (pBR322-trp); lpp promoter (the pIN-series); lambda-pP or pR promoters (pOTS); or hybrid promoters such as ptac (pDR540). See Brosius, et al. (1988) "Expression Vectors Employing Lambda-, trp-, lac-, and lpp-derived Promoters", in Rodriguez and Denhardt (eds.) *Vectors: A Survey of Molecular Cloning Vectors and Their Uses* 10:205–236 Buttersworth, Boston, Mass.

Lower eukaryotes, e.g., yeasts and *Dictyostelium*, may be transformed with CCL28 or CCL27 chemokine sequence containing vectors. For purposes of this invention, the most common lower eukaryotic host is the baker's yeast, *Saccharomyces cerevisiae*. It will be used generically to represent lower eukaryotes although a number of other strains and species are also available. Yeast vectors typically consist of a replication origin (unless of the integrating type), a selection gene, a promoter, DNA encoding the desired protein or its fragments, and sequences for translation termination, polyadenylation, and transcription termination. Suitable expression vectors for yeast include such constitutive promoters as 3-phosphoglycerate kinase and various other glycolytic enzyme gene promoters or such inducible promoters as the alcohol dehydrogenase 2 promoter or metallothionine promoter. Suitable vectors include derivatives of the following types: self-replicating low copy number (such as the YRp-series), self-replicating high copy number (such as the YEp-series); integrating types (such as the YIp-series), or mini-chromosomes (such as the YCp-series).

Higher eukaryotic tissue culture cells are typically the preferred host cells for expression of the functionally active CCL28 or CCL27 chemokine protein. In principle, many higher eukaryotic tissue culture cell lines may be used, e.g., insect baculovirus expression systems, whether from an invertebrate or vertebrate source. However, mammalian cells are preferred to achieve proper processing, both cotranslationally and posttranslationally. Transformation or transfection and propagation of such cells is routine. Useful cell lines include HeLa cells, Chinese hamster ovary (CHO) cell lines, baby rat kidney (BRK) cell lines, insect cell lines, bird cell lines, and monkey (COS) cell lines. Expression vectors for such cell lines usually include an origin of replication, a promoter, a translation initiation site, RNA splice sites (e.g., if genomic DNA is used), a polyadenylation site, and a transcription termination site. These vectors also may contain a selection gene or amplification gene. Suitable expression vectors may be plasmids, viruses, or retroviruses carrying promoters derived, e.g., from such sources as from adenovirus, SV40, parvoviruses, vaccinia virus, or cytomegalovirus. Representative examples of suitable expression vectors include pCDNA1; pCD, see Okayama, et al. (1985) *Mol. Cell Biol.* 5:1136–1142; pMC1neo Poly-A, see Thomas, et al. (1987) *Cell* 51:503–512; and a baculovirus vector such as pAC 373 or pAC 610.

It is likely that CCL28 or CCL27 chemokines need not be glycosylated to elicit biological responses. However, it will occasionally be desirable to express a CCL28 or CCL27 chemokine polypeptide in a system which provides a specific or defined glycosylation pattern. In this case, the usual pattern will be that provided naturally by the expression system. However, the pattern will be modifiable by exposing the polypeptide, e.g., in unglycosylated form, to appropriate glycosylating proteins introduced into a heterologous expression system. For example, the CCL27 chemokine gene may be co-transformed with one or more genes encoding mammalian or other glycosylating enzymes. It is further understood that over glycosylation may be detrimental to CCL27 chemokine biological activity, and that one of skill may perform routine testing to optimize the degree of glycosylation which confers optimal biological activity.

A CCL28 or CCL27 chemokine, or a fragment thereof, may be engineered to be phosphatidyl inositol (PI) linked to a cell membrane, but can be removed from membranes by treatment with a phosphatidyl inositol cleaving enzyme, e.g., phosphatidyl inositol phospholipase-C. This releases the antigen in a biologically active form, and allows purification by standard procedures of protein chemistry. See, e.g., Low (1989) *Biochem. Biophys. Acta* 988:427–454; Tse, et al. (1985) *Science* 230:1003–1008; and Brunner, et al. (1991) *J. Cell Biol.* 114:1275–1283.

Now that CCL27 and CCL28 chemokines have been characterized, fragments or derivatives thereof can be prepared by conventional processes for synthesizing peptides. These include processes such as are described in Stewart and Young (1984) *Solid Phase Peptide Synthesis* Pierce Chemical Co., Rockford, Ill.; Bodanszky and Bodanszky (1984) *The Practice of Peptide Synthesis* Springer-Verlag, New York, N.Y.; and Bodanszky (1984) *The Principles of Peptide Synthesis* Springer-Verlag, New York, N.Y. For example, an azide process, an acid chloride process, an acid anhydride process, a mixed anhydride process, an active ester process (for example, p-nitrophenyl ester, N-hydroxysuccinimide ester, or cyanomethyl ester), a carbodiimidazole process, an oxidative-reductive process, or a dicyclohexylcarbodiimide (DCCD)/additive process can be used. Solid phase and solution phase syntheses are both applicable to the foregoing processes. See also chemical ligation, e.g., Dawson, et al. (1994) *Science* 266:776–779, a method of linking long synthetic peptides by a peptide bond.

The prepared protein and fragments thereof can be isolated and purified from the reaction mixture by means of peptide separation, for example, by extraction, precipitation, electrophoresis and various forms of chromatography, and the like. The CCL28 or CCL27 chemokines of this invention can be obtained in varying degrees of purity depending upon its desired use. Purification can be accomplished by use of known protein purification techniques or by the use of the antibodies or binding partners herein described, e.g., in immunoabsorbant affinity chromatography. This immunoabsorbant affinity chromatography is carried out by first linking the antibodies to a solid support and then contacting the linked antibodies with solubilized lysates of appropriate source cells, lysates of other cells expressing the ligand, or lysates or supernatants of cells producing the CCL28 or CCL27 chemokines as a result of recombinant DNA techniques, see below.

Multiple cell lines may be screened for one which expresses a CCL27 chemokine at a high level compared with other cells. Natural CCL28 or CCL27 chemokines can be isolated from natural sources, or by expression from a transformed cell using an appropriate expression vector. Purification of the expressed protein is achieved by standard procedures, or may be combined with engineered means for effective purification at high efficiency from cell lysates or supernatants. Epitope or other tags, e.g., FLAG or $His_6$ segments, can be used for such purification features.

V. Antibodies

Antibodies can be raised to various CCL28 or CCL27 chemokines, including individual, polymorphic, allelic, strain, or species variants, and fragments thereof, both in their naturally occurring (full-length) forms and in their recombinant forms. Additionally, antibodies can be raised to CCL28 or CCL27 chemokines in either their active forms or in their inactive forms. Anti-idiotypic antibodies may also be used. The antibodies may exhibit various binding specificities for species, individual or polymorphic variants A. Antibody Production A number of immunogens may be used to produce antibodies specifically reactive with CCL28 or CCL27 chemokine proteins. Recombinant protein is the preferred immunogen for the production of monoclonal or polyclonal antibodies. Naturally occurring protein may also be used either in pure or impure form. Synthetic peptides, made using the CCL28 or CCL27 chemokine protein sequences described herein, may also used as an immunogen for the production of antibodies to CCL28 or CCL27 chemokines. Recombinant protein can be expressed in eukaryotic or prokaryotic cells as described herein, and purified as described. Naturally folded or denatured material can be used, as appropriate, for producing antibodies. Either monoclonal or polyclonal antibodies may be generated for subsequent use in immunoassays to measure the protein.

Methods of producing polyclonal antibodies are known to those of skill in the art. Typically, an immunogen, preferably a purified protein, is mixed with an adjuvant and animals are immunized with the mixture. The animal's immune response to the immunogen preparation is monitored by taking test bleeds and determining the titer of reactivity to the CCL28 or CCL27 chemokine protein of interest. When appropriately high titers of antibody to the immunogen are obtained, usually after repeated immunizations, blood is collected from the animal and antisera are prepared. Further fractionation of the antisera to enrich for antibodies reactive to the protein can be done if desired. See, e.g., Harlow and Lane; or Coligan.

Monoclonal antibodies may be obtained by various techniques familiar to those skilled in the art. Typically, spleen cells from an animal immunized with a desired antigen are immortalized, commonly by fusion with a myeloma cell (see, Kohler and Milstein (1976) *Eur. J. Immunol.* 6:511–519, incorporated herein by reference). Alternative methods of immortalization include transformation with Epstein Barr Virus, oncogenes, or retroviruses, or other methods known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according, e.g., to the general protocol outlined by Huse, et al. (1989) *Science* 246:1275–1281.

Antibodies, including binding fragments and single chain versions, against predetermined fragments of CCL27 chemokines can be raised by immunization of animals with conjugates of the fragments with carrier proteins as described above. Monoclonal antibodies are prepared from cells secreting the desired antibody. These antibodies can be screened for binding to normal or defective CCL28 or CCL27 chemokines, or screened for agonistic or antagonistic activity, e.g., mediated through a receptor. These monoclonal antibodies will usually bind with at least a $K_D$ of about 1 mM, more usually at least about 300 µM, typically at least about 10 µM, more typically at least about 30 µM, preferably at least about 10 µM, and more preferably at least about 3 µM or better.

In some instances, it is desirable to prepare monoclonal antibodies from various mammalian hosts, such as mice, rodents, primates, humans, etc. Description of techniques for preparing such monoclonal antibodies may be found in, e.g., Stites, et al. (eds.) *Basic and Clinical Immunology* (4th ed.) Lange Medical Publications, Los Altos, Calif., and references cited therein; Harlow and Lane (1988) *Antibodies: A Laboratory Manual* CSH Press; Goding (1986) *Monoclonal Antibodies: Principles and Practice* (2d ed.) Academic Press, New York, N.Y.; and particularly in Kohler and Milstein (1975) *Nature* 256:495–497, which discusses one method of generating monoclonal antibodies. Summarized briefly, this method involves injecting an animal with an immunogen. The animal is then sacrificed and cells taken from its spleen, which are then fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Other suitable techniques involve selection of libraries of antibodies in phage or similar vectors. See, e.g., Huse, et al. (1989) "Generation of a Large Combinatorial Library of the Immunoglobulin Repertoire in Phage Lambda," *Science* 246:1275–1281; and Ward, et al. (1989) *Nature* 341:544–546. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced. See, Cabilly, U.S. Pat. No. 4,816,567; and Queen, et al. (1989) *Proc. Nat'l Acad. Sci. USA* 86:10029–10033.

The antibodies of this invention are useful for affinity chromatography in isolating CCL28 or CCL27 chemokine protein. Columns can be prepared where the antibodies are linked to a solid support, e.g., particles, such as agarose, SEPHADEX, or the like, where a cell lysate or supernatant may be passed through the column, the column washed, followed by increasing concentrations of a mild denaturant, whereby purified CCL28 or CCL27 chemokine protein will be released. Likewise, antibody binding to the chemokine may be capable of neutralizing receptor binding, and may serve as a receptor antagonist. They may also be useful as Western blot detection reagents, or ELISA reagents.

The antibodies may also be used to screen expression libraries for particular expression products. Usually the antibodies used in such a procedure will be labeled with a moiety allowing easy detection of presence of antigen by antibody binding.

Antibodies to CCL28 or CCL27 chemokines may be used for the identification of cell populations expressing CCL28 or CCL27 chemokines. By assaying the expression products of cells expressing, e.g., CCL27 chemokines it is possible to diagnose disease, e.g., immune-compromised conditions.

Antibodies raised against each CCL28 or CCL27 chemokine will also be useful to raise anti-idiotypic antibodies. These will be useful in detecting or diagnosing various immunological conditions related to expression of the antigens.

B. Immunoassays

A particular protein can be measured by a variety of immunoassay methods. For a review of immunological and immunoassay procedures in general, see Stites and Terr (eds.) (1991) *Basic and Clinical Immunology* (7th ed.). Moreover, the immunoassays of the present invention can be performed in many configurations, which are reviewed extensively in Maggio (ed.) (1980) *Enzyme Immunoassay* CRC Press, Boca Raton, Fla.; Tijan (1985) "Practice and Theory of Enzyme Immunoassays," *Laboratory Techniques in Biochemistry and Molecular Biology*, Elsevier Science Publishers B.V., Amsterdam; and Harlow and Lane *Antibodies, A Laboratory Manual*, supra, each of which is incorporated herein by reference. See also Chan (ed.) (1987)

*Immunoassay: A Practical Guide* Academic Press, Orlando, Fla.; Price and Newman (eds.) (1991) *Principles and Practice of Immunoassays* Stockton Press, NY; and Ngo (ed.) (1988) *Non-isotopic Immunoassays* Plenum Press, NY.

Immunoassays for measurement of, e.g., CCL28 chemokine proteins can be performed by a variety of methods known to those skilled in the art. In brief, immunoassays to measure the protein can be either competitive or noncompetitive binding assays. In competitive binding assays, the sample to be analyzed competes with a labeled analyte for specific binding sites on a capture agent bound to a solid surface. Preferably the capture agent is an antibody specifically reactive with CCL28 chemokine proteins produced as described above. The concentration of labeled analyte bound to the capture agent is inversely proportional to the amount of free analyte present in the sample.

In a competitive binding immunoassay, the CCL28 chemokine protein present in the sample competes with labeled protein for binding to a specific binding agent, for example, an antibody specifically reactive with the CCL28 chemokine protein. The binding agent may be bound to a solid surface to effect separation of bound labeled protein from the unbound labeled protein. Alternately, the competitive binding assay may be conducted in liquid phase and a variety of techniques known in the art may be used to separate the bound labeled protein from the unbound labeled protein. Following separation, the amount of bound labeled protein is determined. The amount of protein present in the sample is inversely proportional to the amount of labeled protein binding.

Alternatively, a homogeneous immunoassay may be performed in which a separation step is not needed. In these immunoassays, the label on the protein is altered by the binding of the protein to its specific binding agent. This alteration in the labeled protein results in a decrease or increase in the signal emitted by label, so that measurement of the label at the end of the immunoassay allows for detection or quantitation of the protein.

CCL28 or CCL27 chemokine proteins may also be determined by a variety of noncompetitive immunoassay methods. For example, a two-site, solid phase sandwich immunoassay may be used. In this type of assay, a binding agent for the protein, for example an antibody, is attached to a solid support. A second protein binding agent, which may also be an antibody, and which binds the protein at a different site, is labeled. After binding at both sites on the protein has occurred, the unbound labeled binding agent is removed and the amount of labeled binding agent bound to the solid phase is measured. The amount of labeled binding agent bound is directly proportional to the amount of protein in the sample.

Western blot analysis can be used to determine the presence of, e.g., CCL27 chemokine proteins in a sample. Electrophoresis is carried out, for example, on a tissue sample suspected of containing the protein. Following electrophoresis to separate the proteins, and transfer of the proteins to a suitable solid support, e.g., a nitrocellulose filter, the solid support is incubated with an antibody reactive with the protein. This antibody may be labeled, or alternatively may be detected by subsequent incubation with a second labeled antibody that binds the primary antibody.

The immunoassay formats described above employ labeled assay components. The label may be coupled directly or indirectly to the desired component of the assay according to methods well known in the art. A wide variety of labels and methods may be used. Traditionally, a radioactive label incorporating $3_H$, $125_I$, $35_S$, $14_C$, or $32_P$ was used. Non-radioactive labels include ligands which bind to labeled antibodies, fluorophores, chemiluminescent agents, enzymes, and antibodies which can serve as specific binding pair members for a labeled ligand. The choice of label depends on sensitivity required, ease of conjugation with the compound, stability requirements, and available instrumentation. For a review of various labeling or signal producing systems which may be used, see U.S. Pat. No. 4,391,904, which is incorporated herein by reference.

Antibodies reactive with a particular protein can also be measured by a variety of immunoassay methods. For a review of immunological and immunoassay procedures applicable to the measurement of antibodies by immunoassay techniques, see Stites and Terr (eds.) *Basic and Clinical Immunology* (7th ed.) supra; Maggio (ed.) *Enzyme Immunoassay*, supra; and Harlow and Lane *Antibodies, A Laboratory Manual*, supra.

In brief, immunoassays to measure antisera reactive with, e.g., CCL28 chemokine proteins can be either competitive or noncompetitive binding assays. In competitive binding assays, the sample analyte competes with a labeled analyte for specific binding sites on a capture agent bound to a solid surface. Preferably the capture agent is a purified recombinant CCL28 chemokine protein produced as described above. Other sources of CCL28 chemokine proteins, including isolated or partially purified naturally occurring protein, may also be used. Noncompetitive assays include sandwich assays, in which the sample analyte is bound between two analyte-specific binding reagents. One of the binding agents is used as a capture agent and is bound to a solid surface. The second binding agent is labeled and is used to measure or detect the resultant complex by visual or instrument means. A number of combinations of capture agent and labeled binding agent can be used. A variety of different immunoassay formats, separation techniques, and labels can be also be used similar to those described above for the measurement of CCL27 chemokine proteins.

VI. Purified CCL28 or CCL27 Chemokines

Human CCL28 nucleotide and amino acid sequence is provided in SEQ ID NO: 1 and 2. Human CCL27 nucleotide and amino acid sequence is provided in SEQ ID NO: 5 and 6; mouse CCL27 nucleotide and amino acid sequence is provided in SEQ ID NO: 7 and 8.

Purified protein or defined peptides are useful for generating antibodies by standard methods, as described above. Synthetic peptides or purified protein can be presented to an immune system to generate polyclonal and monoclonal antibodies. See, e.g., Coligan (1991) *Current Protocols in Immunology* Wiley/Greene, NY; and Harlow and Lane (1989) *Antibodies: A Laboratory Manual* Cold Spring Harbor Press, NY, which are incorporated herein by reference. Alternatively, a CCL28 or CCL27 chemokine receptor can be useful as a specific binding reagent, and advantage can be taken of its specificity of binding, for, e.g., purification of a CCL27 chemokine ligand.

The specific binding composition can be used for screening an expression library made from a cell line which expresses a CCL27 chemokine. Many methods for screening are available, e.g., standard staining of surface expressed ligand, or by panning. Screening of intracellular expression can also be performed by various staining or immunofluorescence procedures. The binding compositions could be used to affinity purify or sort out cells expressing the ligand.

The peptide segments, along with comparison to homologous genes, can also be used to produce appropriate oligonucleotides to screen a library. The genetic code can be used to select appropriate oligonucleotides useful as probes for screening. In combination with polymerase chain reaction (PCR) techniques, synthetic oligonucleotides will be useful in selecting desired clones from a library, including natural allelic an polymorphic variants.

The peptide sequences allow preparation of peptides to generate antibodies to recognize such segments, and allow preparation of oligonucleotides which encode such sequences. The sequence also allows for synthetic preparation, e.g., see Dawson, et al. (1994) *Science* 266:776–779. Since CCL27 and CCL28 chemokines may be secreted proteins, the gene will normally possess an N-terminal signal sequence, which is removed upon processing and secretion. However, the exact processing point may be vary in different cell types, and forms of different lengths are often detected. Prediction of the signal cleavage point can be performed, e.g., using the methods of Nielsen, et al. (1997) *Protein Eng.* 10:1–8. Analysis of the structural features in comparison with the most closely related reported sequences has revealed similarities with other cytokines, particularly the class of proteins known as CC and CXC chemokines.

VII. Physical Variants

This invention also encompasses proteins or peptides having substantial amino acid sequence similarity with an amino acid sequence of a CCL28 or CCL27 chemokine. Natural variants include individual, polymorphic, allelic, strain, or species variants.

Amino acid sequence similarity, or sequence identity, is determined by optimizing residue matches, if necessary, by introducing gaps as required. This changes when considering conservative substitutions as matches. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. Homologous amino acid sequences include natural polymorphic, allelic, and interspecies variations in the protein sequence. Typical homologous proteins or peptides will have from 50–100% similarity (if gaps can be introduced), to 75–100% similarity (if conservative substitutions are included) with the amino acid sequence of the CCL27 chemokine. Similarity measures will be at least about 50%, generally at least 60%, more generally at least 65%, usually at least 70%, more usually at least 75%, preferably at least 80%, and more preferably at least 80%, and in particularly preferred embodiments, at least 85% or more. See also Needleham, et al. (1970) *J. Mol. Biol.* 48:443–453; Sankoff, et al. (1983) *Time Warps, String Edits, and Macromolecules: The Theory and Practice of Sequence Comparison* Chapter One, Addison-Wesley, Reading, Mass.; and software packages from IntelliGenetics, Mountain View, Calif.; and the University of Wisconsin Genetics Computer Group, Madison, Wis.

Nucleic acids encoding mammalian CCL28 chemokine proteins will typically hybridize to the nucleic acid sequence of SEQ ID NO: 1 under stringent conditions. For example, nucleic acids encoding CCL28 chemokine proteins will normally hybridize to the nucleic acid of SEQ ID NO: 1 under stringent hybridization conditions. Generally, stringent conditions are selected to be about 10° C. lower than the thermal melting point (Tm) for the probe sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.2 molar at pH 7 and the temperature is at least about 50° C. Other factors may significantly affect the stringency of hybridization, including, among others, base composition and size of the complementary strands, the presence of organic solvents such as formamide, and the extent of base mismatching. A preferred embodiment will include nucleic acids which will bind to disclosed sequences in 50% formamide and 200 mM NaCl at 42° C.

An isolated CCL27 chemokine DNA can be readily modified by nucleotide substitutions, nucleotide deletions, nucleotide insertions, and short inversions of nucleotide stretches. These modifications result in novel DNA sequences which encode CCL28 or CCL27 chemokine antigens, their derivatives, or proteins having highly similar physiological, immunogenic, or antigenic activity.

Modified sequences can be used to produce mutant antigens or to enhance expression. Enhanced expression may involve gene amplification, increased transcription, increased translation, and other mechanisms. Such mutant CCL27 chemokine derivatives include predetermined or site-specific mutations of the protein or its fragments. "Mutant CCL27 chemokine" encompasses a polypeptide otherwise falling within the homology definition of the human CCL27 chemokine as set forth above, but having an amino acid sequence which differs from that of a CCL27 chemokine as found in nature, whether by way of deletion, substitution, or insertion. In particular, "site specific mutant CCL27 chemokine" generally includes proteins having significant similarity with a protein having a sequence of SEQ ID NO: 6 or 8, e.g., natural embodiments, and as sharing various biological activities, e.g., antigenic or immunogenic, with those sequences, and in preferred embodiments contain most or all of the disclosed sequence. This applies also to polymorphic variants from different individuals. Similar concepts apply to different CCL28 or CCL27 chemokine proteins, particularly those found in various warm blooded animals, e.g., mammals and birds. As stated before, it is emphasized that descriptions are generally meant to encompass other CCL28 or CCL27 chemokine proteins, not limited to the mouse or human embodiments specifically discussed.

Although site specific mutation sites are predetermined, mutants need not be site specific. For example, CCL27 chemokine mutagenesis can be conducted by making amino acid insertions or deletions. Substitutions, deletions, insertions, or any combinations may be generated to arrive at a final construct. Insertions include amino- or carboxyl-terminal fusions, e.g. epitope tags. Random mutagenesis can be conducted at a target codon and the expressed mutants can then be screened for the desired activity. Methods for making substitution mutations at predetermined sites in DNA having a known sequence are well known in the art, e.g., by M13 primer mutagenesis or polymerase chain reaction (PCR) techniques. See also, Sambrook, et al. (1989) and Ausubel, et al. (1987 and Supplements). The mutations in the DNA normally should not place coding sequences out of reading frames and preferably will not create complementary regions that could hybridize to produce secondary mRNA structure such as loops or hairpins.

The present invention also provides recombinant proteins, e.g., heterologous fusion proteins using segments from these proteins. A heterologous fusion protein is a fusion of proteins or segments which are naturally not normally fused in the same manner. Thus, the fusion product of an immunoglobulin with a CCL27 chemokine polypeptide is a continuous protein molecule having sequences fused in a typical peptide linkage, typically made as a single translation product and exhibiting properties derived from each source peptide. A similar concept applies to heterologous nucleic acid sequences.

In addition, new constructs may be made from combining similar functional domains from other proteins. For example, protein-binding or other segments may be "swapped" between different new fusion polypeptides or fragments. See, e.g., Cunningham, et al. (1989) *Science* 243:1330–1336; and O'Dowd, et al. (1988) *J. Biol. Chem.* 263:15985–15992. Thus, new chimeric polypeptides exhibiting new combinations of specificities will result from the functional linkage of protein-binding specificities and other functional domains.

VIII. Binding Agent: Chemokine Protein Complexes

A CCL28 or CCL27 chemokine protein that specifically, or selectively, binds to or that is specifically immunoreactive with an antibody generated against a defined immunogen, such as an immunogen consisting of the amino acid sequence of SEQ ID NO: 2 or 8, is typically determined in an immunoassay. The immunoassay uses a polyclonal antiserum which was raised to a protein of SEQ ID NO: 2, 6, or 8. This antiserum is selected to have low crossreactivity against other chemokines and any such crossreactivity is removed by immunoabsorption prior to use in the immunoassay.

In order to produce antisera for use in an immunoassay, the protein of SEQ ID NO: 2 or 6 or 8, is isolated as described herein. For example, recombinant protein may be produced in a mammalian cell line. An inbred strain of mice such as BALB/c is immunized with the protein of SEQ ID NO: 2 or 6 or 8, using a standard adjuvant, such as Freund's adjuvant, and a standard mouse immunization protocol (see Harlow and Lane, supra). Alternatively, a synthetic peptide, preferably near full length, derived from the sequences disclosed herein and conjugated to a carrier protein can be used an immunogen. Polyclonal sera are collected and titered against the immunogen protein in an immunoassay, for example, a solid phase immunoassay with the immunogen immobilized on a solid support. Polyclonal antisera with a titer of $10^4$ or greater are selected and tested for their cross reactivity against C, CC, CX3C, and CXC chemokines, using a competitive binding immunoassay such as the one described in Harlow and Lane, supra, at pages 570–573. Preferably two chemokines are used in this determination in conjunction with human CCL27 chemokine.

Immunoassays in the competitive binding format can be used for the crossreactivity determinations. For example, a protein of SEQ ID NO: 2 or of SEQ ID NO: 6 and/or 8 can be immobilized to a solid support. Proteins added to the assay compete with the binding of the antisera to the immobilized antigen. The ability of the above proteins to compete with the binding of the antisera to the immobilized protein is compared to the protein of SEQ ID NO: 2 or of SEQ ID NO: 6 and/or 8. The percent crossreactivity for the above proteins is calculated, using standard calculations. Those antisera with less than 10% crossreactivity with each of the proteins listed above are selected and pooled. The cross-reacting antibodies are then removed from the pooled antisera by immunoabsorption with the above-listed proteins.

The immunoabsorbed and pooled antisera are then used in a competitive binding immunoassay as described above to compare a second protein to the immunogen protein (e.g., the CCL27 chemokine motif of SEQ ID NO: 6 or 8). In order to make this comparison, the two proteins are each assayed at a wide range of concentrations and the amount of each protein required to inhibit 50% of the binding of the antisera to the immobilized protein is determined. If the amount of the second protein required is less than twice the amount of the protein, e.g., of SEQ ID NO: 6 or 8 that is required, then the second protein is said to specifically bind to an antibody generated to the immunogen.

It is understood that CCL27 chemokine protein is a species form of a group of homologous proteins across species that include closely related genes. For a particular gene product, such as the CCL27 chemokine protein, the term refers not only to the amino acid sequences disclosed herein, but also to other proteins that are polymorphic, allelic, or non-allelic variants. It is also understood that the term "CCL27" includes nonnatural mutations introduced by deliberate mutation using conventional recombinant technology such as single site mutation, or by excising short sections of DNA encoding CCL27 chemokine proteins, or by substituting new amino acids, or adding new amino acids. Such minor alterations should substantially maintain the immunoidentity of the original molecule and/or its biological activity. Thus, these alterations include proteins that are specifically immunoreactive with a designated naturally occurring CCL27 chemokine protein, for example, the CCL27 chemokine protein shown in SEQ ID NO: 6 or 8. The biological properties of the altered proteins can be determined by expressing the protein in an appropriate cell line and measuring an appropriate biological activity, e.g., a chemotactic effect. Particular protein modifications considered minor would include conservative substitution of amino acids with similar chemical properties, as described above for the CCL27 chemokine as a whole. By aligning a protein optimally with the protein of SEQ ID NO: 6 or 8, and by using the conventional immunoassays described herein to determine immunoidentity, or by using lymphocyte chemotaxis assays, one can determine the protein compositions of the invention.

IX. Functional Variants

The blocking of physiological response to CCL28 or CCL27 chemokine may result from the inhibition of binding of the protein to its receptor, e.g., through competitive inhibition. Thus, in vitro assays of the present invention will often use isolated protein, membranes from cells expressing a recombinant membrane associated CCL28 or CCL27 chemokine, soluble fragments comprising receptor binding segments of these proteins, or fragments attached to solid phase substrates. These assays will also allow for the diagnostic determination of the effects of either binding segment mutations and modifications, or protein mutations and modifications, e.g., protein analogs. This invention also contemplates the use of competitive drug screening assays, e.g., where neutralizing antibodies to antigen or receptor fragments compete with a test compound for binding to the protein. In this manner, the antibodies can be used to detect the presence of a polypeptide which shares one or more antigenic binding sites of the protein and can also be used to occupy binding sites on the protein that might otherwise interact with a receptor.

"Derivatives" of, e.g., CCL27 chemokine antigens include amino acid sequence mutants, glycosylation variants, and covalent or aggregate conjugates with other chemical moieties. Covalent derivatives can be prepared by linkage of functionalities to groups which are found in CCL27 chemokine amino acid side chains or at the N- or C-termini, by means which are well known in the art. These derivatives can include, without limitation, aliphatic esters or amides of the carboxyl terminus, or of residues containing carboxyl side chains, O-acyl derivatives of hydroxyl group-containing residues, and N-acyl derivatives of the amino terminal amino acid or amino-group containing residues, e.g., lysine or arginine. Acyl groups are selected from the group of alkyl-moieties including, e.g., C3 to C18 normal alkyl, thereby forming alkanoyl aroyl species. Covalent attachment to carrier proteins may be important when immunogenic moieties are haptens.

In particular, glycosylation alterations are included, e.g., made by modifying the glycosylation patterns of a polypeptide during its synthesis and processing, or in further processing steps. Particularly preferred means for accomplishing this are by exposing the polypeptide to glycosylating enzymes derived from cells which normally provide such processing, e.g., mammalian glycosylation enzymes. Deglycosylation enzymes are also contemplated. Also embraced are versions of the same primary amino acid sequence which have other minor modifications, including phosphorylated amino acid residues, e.g., phosphotyrosine, phosphoserine, or phosphothreonine, or other moieties, including ribosyl groups or cross-linking reagents.

A major group of derivatives are covalent conjugates of the CCL27 chemokine or fragments thereof with other proteins or polypeptides. These derivatives can be synthesized in recombinant culture such as N- or C-terminal fusions or by the use of agents known in the art for their usefulness in cross-linking proteins through reactive side groups. Preferred protein derivatization sites with cross-linking agents are at free amino groups, carbohydrate moieties, and cysteine residues.

Fusion polypeptides between CCL27 chemokine and other homologous or heterologous proteins are also provided. Many growth factors and cytokines are homodimeric entities, and a repeat construct may have various advantages, including lessened susceptibility to proteolytic degradation. Moreover, many receptors require ligand dimerization to transduce a signal, and various dimeric proteins or domain repeats can be desirable. Heterologous polypeptides may be fusions between different surface markers, resulting in, e.g., a hybrid protein exhibiting receptor binding specificity. Likewise, heterologous fusions may be constructed which would exhibit a combination of properties or activities of the derivative proteins. Typical examples are fusions of a reporter polypeptide, e.g., luciferase, with a segment or domain of a protein, e.g., a receptor-binding segment, so that the presence or location of the fused protein may be easily determined. See, e.g., Dull, et al., U.S. Pat. No. 4,859,609. Other gene fusion partners include bacterial β-galactosidase, trpE, Protein A, β-lactamase, alpha amylase, alcohol dehydrogenase, and yeast alpha mating factor. See, e.g., Godowski, et al. (1988) *Science* 241:812–816.

Such polypeptides may also have amino acid residues which have been chemically modified by phosphorylation, sulfonation, biotinylation, or the addition or removal of other moieties, particularly those which have molecular shapes similar to phosphate groups. In some embodiments, the modifications will be useful labeling reagents, or serve as purification targets, e.g., affinity ligands.

This invention also contemplates the use of derivatives of CCL27 chemokine other than variations in amino acid sequence or glycosylation. Such derivatives may involve covalent or aggregative association with chemical moieties. These derivatives generally fall into the three classes: (1) salts, (2) side chain and terminal residue covalent modifications, and (3) adsorption complexes, for example with cell membranes. Such covalent or aggregative derivatives are useful as immunogens, as reagents in immunoassays, or in purification methods such as for affinity purification of ligands or other binding ligands. For example, a CCL27 chemokine antigen can be immobilized by covalent bonding to a solid support such as cyanogen bromide-activated SEPHAROSE, by methods which are well known in the art, or adsorbed onto polyolefin surfaces, with or without glutaraldehyde cross-linking, for use in the assay or purification of anti-CCL27 chemokine antibodies or its receptor. The CCL27 chemokine can also be labeled with a detectable group, e.g., radioiodinated by the chloramine T procedure, covalently bound to rare earth chelates, or conjugated to another fluorescent moiety for use in diagnostic assays. Purification of CCL27 chemokines may be effected by immobilized antibodies or receptor.

Isolated CCL27 chemokine genes will allow transformation of cells lacking expression of corresponding CCL27 chemokine, e.g., either species types or cells which lack corresponding proteins and exhibit negative background activity. Expression of transformed genes will allow isolation of antigenically pure cell lines, with defined or single specie variants. This approach will allow for more sensitive detection and discrimination of the physiological effects of CCL27 chemokine receptor proteins. Subcellular fragments, e.g., cytoplasts or membrane fragments, can be isolated and used. Descriptions using CCL27 as an example will generally be alternatively applicable to the CCL28.

X. Uses

The present invention provides reagents which will find use in diagnostic applications as described elsewhere herein, e.g., in the general description for developmental abnormalities, or below in the description of kits for diagnosis.

CCL27 chemokine nucleotides, e.g., CCL27 chemokine DNA or RNA, may be used as a component in a forensic assay. For instance, the nucleotide sequences provided may be labeled using, e.g., $^{32}P$ or biotin and used to probe standard restriction fragment polymorphism blots, providing a measurable character to aid in distinguishing between individuals or, e.g., species sources. Such probes may be used in well-known forensic techniques such as genetic fingerprinting. In addition, nucleotide probes made from CCL27 chemokine sequences may be used in in situ assays to detect chromosomal abnormalities. For instance, rearrangements in the human chromosome encoding a CCL27 chemokine gene may be detected via well-known in situ techniques, using CCL27 chemokine probes in conjunction with other known chromosome markers.

Antibodies and other binding agents directed towards CCL27 chemokine proteins or nucleic acids may be used to purify the corresponding CCL27 chemokine molecule. As described in the Examples below, antibody purification of CCL27 chemokine components is both possible and practicable. Antibodies and other binding agents may also be used in a diagnostic fashion to determine whether CCL27 chemokine components are present in a tissue sample or cell population using well-known techniques described herein. The ability to attach a binding agent to a CCL27 chemokine provides a means to diagnose disorders associated with CCL27 chemokine misregulation. Antibodies and other CCL27 chemokine binding agents may also be useful as histological markers. As described in the examples below, CCL27 chemokine expression is limited to specific tissue types. By directing a probe, such as an antibody or nucleic acid to a CCL27 chemokine it is possible to use the probe to distinguish tissue and cell types in situ or in vitro.

This invention also provides reagents with significant therapeutic value. The CCL27 chemokine (naturally occurring or recombinant), fragments thereof, and antibodies thereto, along with compounds identified as having binding affinity to a CCL27 chemokine, are useful in the treatment of conditions associated with abnormal physiology or development, including abnormal proliferation, e.g., cancerous conditions, or degenerative conditions. Abnormal proliferation, regeneration, degeneration, and atrophy may be modulated by appropriate therapeutic treatment using the compositions provided herein. For example, a disease or disorder associated with abnormal expression or abnormal signaling by a CCL27 chemokine is a target for an agonist or antagonist of the protein. The proteins likely play a role in regulation or development of neuronal or hematopoietic cells, e.g., lymphoid cells, which affect immunological responses.

Other abnormal developmental conditions are known in cell types shown to possess CCL28 or CCL27 chemokine mRNA by northern blot analysis. See Berkow (ed.) *The Merck Manual of Diagnosis and Therapy*, Merck & Co., Rahway, N.J.; and Thorn, et al. *Harrison's Principles of Internal Medicine*, McGraw-Hill, N.Y. Developmental or functional abnormalities, e.g., of the neuronal or immune system, cause significant medical abnormalities and conditions which may be susceptible to prevention or treatment using compositions provided herein.

Certain chemokines have also been implicated in viral replication mechanisms. See, e.g., Cohen (1996) *Science* 272:809–810; Feng, et al. (1996) *Science* 272:872–877; and Cocchi, et al. (1995) *Science* 270:1811–1816. The CCL28 or CCL27 chemokine may be useful in a similar context.

Recombinant CCL28 or CCL27 chemokine or chemokine antibodies can be purified and then administered to a patient. These reagents can be combined for therapeutic use with additional active or inert ingredients, e.g., in conventional pharmaceutically acceptable carriers or diluents, e.g., immunogenic adjuvants, along with physiologically innocuous stabilizers and excipients. These combinations can be sterile filtered and placed into dosage forms as by lyophilization in dosage vials or storage in stabilized aqueous preparations. This invention also contemplates use of antibodies or binding fragments thereof, including forms which are not complement binding.

Drug screening using antibodies or receptor or fragments thereof can identify compounds having binding affinity to CCL28 or CCL27 chemokine, including isolation of associated components. Subsequent biological assays can then be utilized to determine if the compound has intrinsic stimulating activity and is therefore a blocker or antagonist in that it blocks the activity of the protein. Likewise, a compound having intrinsic stimulating activity can activate the receptor and is thus an agonist in that it simulates the activity of, e.g., a CCL27 chemokine. This invention further contemplates the therapeutic use of antibodies to CCL27 chemokine as antagonists. This approach should be particularly useful with other CCL27 chemokine species variants.

The quantities of reagents necessary for effective therapy will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman, et al. (eds.) (1990) *Goodman and Gilman's: The Pharmacological Bases of Therapeutics* (8th ed.) Pergamon Press; and (1990) *Remington's Pharmaceutical Sciences* (17th ed.) Mack Publishing Co., Easton, Pa. Methods for administration are discussed therein and below, e.g., for oral, intravenous, intraperitoneal, or intramuscular administration, transdermal diffusion, and others. Pharmaceutically acceptable carriers will include water, saline, buffers, and other compounds described, e.g., in the *Merck Index*, Merck & Co., Rahway, N.J. Dosage ranges would ordinarily be expected to be in amounts lower than 1 mM concentrations, typically less than about 10 µM concentrations, usually less than about 100 nM, preferably less than about 10 µM (picomolar), and most preferably less than about 1 fM (femtomolar), with an appropriate carrier. Slow release formulations, or a slow release apparatus will often be utilized for continuous administration.

CCL28 or CCL27 chemokines, fragments thereof, and antibodies to it or its fragments, antagonists, and agonists, may be administered directly to the host to be treated or, depending on the size of the compounds, it may be desirable to conjugate them to carrier proteins such as ovalbumin or serum albumin prior to their administration. Therapeutic formulations may be administered in any conventional dosage formulation. While it is possible for the active ingredient to be administered alone, it is preferable to present it as a pharmaceutical formulation. Formulations typically comprise at least one active ingredient, as defined above, together with one or more acceptable carriers thereof. Each carrier should be both pharmaceutically and physiologically acceptable in the sense of being compatible with the other ingredients and not injurious to the patient. Formulations include those suitable for oral, rectal, nasal, or parenteral (including subcutaneous, intramuscular, intravenous and intradermal) administration. The formulations may conveniently be presented in unit dosage form and may be prepared by any methods well known in the art of pharmacy. See, e.g., Gilman, et al. (eds.) (1990) *Goodman and Gilman's: The Pharmacological Bases of Therapeutics* (8th ed.) Pergamon Press; and (1990) *Remington's Pharmaceutical Sciences* (17th ed.) Mack Publishing Co., Easton, Pa.; Avis, et al. (eds.) (1993) *Pharmaceutical Dosage Forms: Parenteral Medications* Dekker, NY; Lieberman, et al. (eds.) (1990) *Pharmaceutical Dosage Forms: Tablets* Dekker, NY; and Lieberman, et al. (eds.) (1990) *Pharmaceutical Dosage Forms: Disperse Systems* Dekker, NY. The therapy of this invention may be combined with or used in association with other therapeutic agents.

Both the naturally occurring and the recombinant forms of the CCL28 or CCL27 chemokines of this invention are particularly useful in kits and assay methods which are capable of screening compounds for binding activity to the proteins. Several methods of automating assays have been developed in recent years so as to permit screening of tens of thousands of compounds in a short period. See, e.g., Fodor, et al. (1991) *Science* 251:767–773, and other descriptions of chemical diversity libraries, which describe means for testing of binding affinity by a plurality of compounds. The development of suitable assays can be greatly facilitated by the availability of large amounts of purified, soluble CCL27 chemokine as provided by this invention.

For example, antagonists can normally be found once the protein has been structurally defined. Testing of potential protein analogs is now possible upon the development of highly automated assay methods using a purified receptor. In particular, new agonists and antagonists will be discovered by using screening techniques described herein. Of particular importance are compounds found to have a combined binding affinity for multiple CCL27 chemokine receptors, e.g., compounds which can serve as antagonists for species variants of a CCL27 chemokine.

This invention is particularly useful for screening compounds by using recombinant protein in a variety of drug screening techniques. The advantages of using a recombinant protein in screening for specific ligands include: (a) improved renewable source of the CCL27 chemokine from a specific source; (b) potentially greater number of ligands per cell giving better signal to noise ratio in assays; and (c) species variant specificity (theoretically giving greater biological and disease specificity).

One method of drug screening utilizes eukaryotic or prokaryotic host cells which are stably transformed with recombinant DNA molecules expressing a chemokine receptor. Cells may be isolated which express a receptor in isolation from any others. Such cells, either in viable or fixed form, can be used for standard ligand/receptor binding assays. See also, Parce, et al. (1989) *Science* 246:243–247; and Owicki, et al. (1990) *Proc. Nat'l Acad. Sci. USA* 87:4007–4011, which describe sensitive methods to detect cellular responses. Competitive assays are particularly useful, where the cells (source of CCL27 chemokine) are contacted and incubated with a labeled receptor or antibody having known binding affinity to the ligand, such as $^{125}$I-antibody, and a test sample whose binding affinity to the binding composition is being measured. The bound and free labeled binding compositions are then separated to assess the degree of ligand binding. The amount of test compound bound is inversely proportional to the amount of labeled receptor binding to the known source. Any one of numerous techniques can be used to separate bound from free ligand to assess the degree of ligand binding. This separation step could typically involve a procedure such as adhesion to filters followed by washing, adhesion to plastic followed by washing, or centrifugation of the cell membranes. Viable cells could also be used to screen for the effects of drugs on CCL27 chemokine mediated functions, e.g., second messenger levels, i.e., $Ca^{++}$; cell proliferation; inositol phosphate pool changes; and others. Some detection methods allow for elimination of a separation step, e.g., a proximity sensitive detection system. Calcium sensitive dyes will be useful for detecting $Ca^{++}$ levels, with a fluorimeter or a fluorescence cell sorting apparatus.

Another method utilizes membranes from transformed eukaryotic or prokaryotic host cells as the source of a CCL27 chemokine. These cells are stably transformed with DNA vectors directing the expression of a CCL27 chemokine, e.g., an engineered membrane bound form. Essentially, the membranes would be prepared from the cells and used in a receptor/ligand binding assay such as the competitive assay set forth above.

Still another approach is to use solubilized, unpurified or solubilized, purified CCL27 chemokine from transformed eukaryotic or prokaryotic host cells. This allows for a "molecular" binding assay with the advantages of increased specificity, the ability to automate, and high drug test throughput.

Another technique for drug screening involves an approach which provides high throughput screening for compounds having suitable binding affinity to a CCL27 chemokine antibody and is described in detail in Geysen, European Patent Application 84/03564, published on Sep. 13, 1984. First, large numbers of different small peptide test compounds are synthesized on a solid substrate, e.g., plastic pins or some other appropriate surface, see Fodor, et al., supra. Then all the pins are reacted with solubilized, unpurified or solubilized, purified CCL27 chemokine antibody, and washed. The next step involves detecting bound CCL27 chemokine antibody.

Rational drug design may also be based upon structural studies of the molecular shapes of the CCL27 chemokine and other effectors or analogs. See, e.g., *Methods in Enzymology* vols. 202 and 203. Effectors may be other proteins which mediate other functions in response to ligand binding, or other proteins which normally interact with the receptor. One means for determining which sites interact with specific other proteins is a physical structure determination, e.g., x-ray crystallography or 2 dimensional NMR techniques. These will provide guidance as to which amino acid residues form molecular contact regions. For a detailed description of protein structural determination, see, e.g., Blundell and Johnson (1976) *Protein Crystallography* Academic Press, NY.

A purified CCL27 chemokine can be coated directly onto plates for use in the aforementioned drug screening techniques. However, non-neutralizing antibodies to these ligands can be used as capture antibodies to immobilize the respective ligand on the solid phase. Examples with CCL27 will alternately be performed with the CCL28 chemokine.

XI. Kits

This invention also contemplates use of CCL28 or CCL27 chemokine proteins, fragments thereof, peptides, and their fusion products in a variety of diagnostic kits and methods for detecting the presence of chemokine or a chemokine receptor. Typically the kit will have a compartment containing either a defined CCL28 or CCL27 chemokine peptide or gene segment or a reagent which recognizes one or the other, e.g., receptor fragments or antibodies.

For example, a kit for determining the binding affinity of a test compound to a CCL27 chemokine would typically comprise a test compound; a labeled compound, e.g., a receptor or antibody having known binding affinity for the CCL27 chemokine; a source of CCL27 chemokine (naturally occurring or recombinant); and a means for separating bound from free labeled compound, such as a solid phase for immobilizing the CCL27 chemokine. Once compounds are screened, those having suitable binding affinity to the CCL27 chemokine can be evaluated in suitable biological assays, as are well known in the art, to determine whether they act as agonists or antagonists to the receptor. The availability of recombinant CCL27 chemokine polypeptides also provide well defined standards for calibrating such assays.

A preferred kit for determining the concentration of, for example, a CCL27 chemokine in a sample would typically comprise a labeled compound, e.g., receptor or antibody, having known binding affinity for the CCL27 chemokine, a source of CCL27 chemokine (naturally occurring or recombinant), and a means for separating the bound from free labeled compound, for example, a solid phase for immobilizing the CCL27 chemokine. Compartments containing reagents, and instructions, will normally be provided.

Antibodies, including antigen binding fragments, specific for the CCL27 chemokine or ligand fragments are useful in diagnostic applications to detect the presence of elevated levels of CCL27 chemokine and/or its fragments. Such diagnostic assays can employ lysates, live cells, fixed cells, immunofluorescence, cell cultures, body fluids, and further can involve the detection of antigens related to the ligand in serum, or the like. Diagnostic assays may be homogeneous (without a separation step between free reagent and antigen-CCL27 chemokine complex) or heterogeneous (with a separation step). Various commercial assays exist, such as radio-immunoassay (RIA), enzyme-linked immunosorbent assay (ELISA), enzyme immunoassay (EIA), enzyme-multiplied immunoassay technique (EMIT), substrate-labeled fluorescent immunoassay (SLFIA), and the like. For example, unlabeled antibodies can be employed by using a second antibody which is labeled and which recognizes the antibody to a CCL27 chemokine or to a particular fragment thereof. Similar assays have also been extensively discussed in the literature. See, e.g., Harlow and Lane (1988) *Antibodies: A Laboratory Manual*, CSH Press, NY; Chan (ed.) (1987) *Immunoassay: A Practical Guide* Academic Press, Orlando, Fla.; Price and Newman (eds.) (1991) *Principles and Practice of Immunoassay* Stockton Press, NY; and Ngo (ed.) (1988) *Nonisotopic Immunoassay* Plenum Press, NY.

Anti-idiotypic antibodies may have similar use to diagnose presence of antibodies against a CCL27 chemokine, as such may be diagnostic of various abnormal states. For example, overproduction of CCL27 chemokine may result in production of various immunological or other medical reactions which may be diagnostic of abnormal physiological states, e.g., in cell growth, activation, or differentiation.

Frequently, the reagents for diagnostic assays are supplied in kits, so as to optimize the sensitivity of the assay. For the subject invention, depending upon the nature of the assay, the protocol, and the label, either labeled or unlabeled antibody or receptor, or labeled CCL27 chemokine is provided. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments for each useful reagent. Desirably, the reagents are provided as a dry lyophilized powder, where the reagents may be reconstituted in an aqueous medium providing appropriate concentrations of reagents for performing the assay.

Many of the aforementioned constituents of the drug screening and the diagnostic assays may be used without modification, or may be modified in a variety of ways. For example, labeling may be achieved by covalently or non-covalently joining a moiety which directly or indirectly provides a detectable signal. In any of these assays, the protein, test compound, CCL27 chemokine, or antibodies thereto can be labeled either directly or indirectly. Possibilities for direct labeling include label groups: radiolabels such as $^{125}$I, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Possibilities for indirect labeling include biotinylation of one constituent followed by binding to avidin coupled to one of the above label groups.

There are also numerous methods of separating the bound from the free ligand, or alternatively the bound from the free test compound. The CCL27 chemokine can be immobilized on various matrices followed by washing. Suitable matrices include plastic such as an ELISA plate, filters, and beads. Methods of immobilizing the CCL27 chemokine to a matrix include, without limitation, direct adhesion to plastic, use of a capture antibody, chemical coupling, and biotin-avidin. The last step in this approach involves the precipitation of ligand/receptor or ligand/antibody complex by any of several methods including those utilizing, e.g., an organic solvent such as polyethylene glycol or a salt such as ammonium sulfate. Other suitable separation techniques include, without limitation, the fluorescein antibody magnetizable particle method described in Rattle, et al. (1984) *Clin. Chem.* 30:1457–1461, and the double antibody magnetic particle separation as described in U.S. Pat. No. 4,659,678.

Methods for linking proteins or their fragments to the various labels have been extensively reported in the literature and do not require detailed discussion here. Many of the techniques involve the use of activated carboxyl groups either through the use of carbodiimide or active esters to form peptide bonds, the formation of thioethers by reaction of a mercapto group with an activated halogen such as chloroacetyl, or an activated olefin such as maleimide, for linkage, or the like. Fusion proteins will also find use in these applications.

Another diagnostic aspect of this invention involves use of oligonucleotide or polynucleotide sequences taken from the sequence of a CCL27 chemokine. These sequences can be used as probes for detecting levels of the CCL27 chemokine message in samples from natural sources, or patients suspected of having an abnormal condition, e.g., cancer or developmental problem. The preparation of both RNA and DNA nucleotide sequences, the labeling of the sequences, and the preferred size of the sequences has received ample description and discussion in the literature. Normally an oligonucleotide probe should have at least about 14 nucleotides, usually at least about 18 nucleotides, and the polynucleotide probes may be up to several kilobases. Various labels may be employed, most commonly radionuclides, particularly $^{32}$P. However, other techniques may also be employed, such as using biotin modified nucleotides for introduction into a polynucleotide. The biotin then serves as the site for binding to avidin or antibodies, which may be labeled with a wide variety of labels, such as radionuclides, fluorophores, enzymes, or the like. Alternatively, antibodies may be employed which can recognize specific duplexes, including DNA duplexes, RNA duplexes, DNA-RNA hybrid duplexes, or DNA-protein duplexes. The antibodies in turn may be labeled and the assay carried out where the duplex is bound to a surface, so that upon the formation of duplex on the surface, the presence of antibody bound to the duplex can be detected. The use of probes to the novel anti-sense RNA may be carried out using many conventional techniques such as nucleic acid hybridization, plus and minus screening, recombinational probing, hybrid released translation (HRT), and hybrid arrested translation (HART). This also includes amplification techniques such as polymerase chain reaction (PCR).

Diagnostic kits which also test for the qualitative or quantitative presence of these and other markers are also contemplated. Diagnosis or prognosis may depend on the combination of multiple indications used as markers. Thus, kits may test for combinations of markers. See, e.g., Viallet, et al. (1989) *Progress in Growth Factor Res.* 1:89–97. Qualitative or quantitative expression of each chemokine may be evaluated by standard methods at the protein or mRNA levels.

XII. Receptor Isolation

Having isolated a binding partner of a specific interaction, methods exist for isolating the counter-partner. See, Gearing, et al. (1989) *EMBO J.* 8:3667–3676. For example, means to label a CCL28 or CCL27 chemokine without interfering with the binding to its receptor can be determined. For example, an affinity label or epitope tag can be fused to either the amino- or carboxyl-terminus of the ligand. An expression library can be screened for specific binding of the CCL28 or CCL27 chemokine, e.g., by cell sorting, or other screening to detect subpopulations which express such a binding component. See, e.g., Ho, et al. (1993) *Proc. Nat'l Acad. Sci. USA* 90:11267–11271. Alternatively, a panning method may be used. See, e.g., Seed and Aruffo (1987) *Proc. Nat'l Acad. Sci. USA* 84:3365–3369. A two-hybrid selection system may also be applied making appropriate constructs with the available chemokine sequences. See, e.g., Fields and Song (1989) *Nature* 340:245–246. Standard $Ca^{++}$ flux methods can also be utilized. See, e.g., Coligan, et al. (eds.) (1992 and periodic supplements) *Current Protocols in Immunology* Greene/Wiley, New York, N.Y.

Protein cross-linking techniques with label can be applied to isolate binding partners of a CCL28 or CCL27 chemokine. This would allow identification of proteins which specifically interact with a CCL28 or CCL27 chemokine, e.g., in a ligand-receptor like manner. Typically, the chemokine family binds to receptors of the seven transmembrane receptor family, and the receptor for the CCL28 or CCL27 chemokine is likely to exhibit a similar structure. Thus, it is likely that the receptor will be found by expression in a system which is capable of expressing such a membrane protein in a form capable of exhibiting ligand binding capability.

The broad scope of this invention is best understood with reference to the following examples, which are not intended to limit the invention to specific embodiments.

EXAMPLES

I. General Methods

Many of the standard methods below are described or referenced, e.g., in Maniatis, et al. (1982) *Molecular Cloning, A Laboratory Manual* Cold Spring Harbor Laboratory, Cold Spring Harbor Press, NY; Sambrook, et al. (1989) *Molecular Cloning: A Laboratory Manual* (2d ed.) Vols. 1–3, CSH Press, NY; Ausubel, et al., *Biology* Greene Publishing Associates, Brooklyn, N.Y.; or Ausubel, et al. (1987 and Supplements) *Current Protocols in Molecular Biology* Wiley/Greene, NY; Innis, et al. (eds.) (1990) *PCR Protocols: A Guide to Methods and Applications* Academic Press, NY. Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification," *Methods in Enzymology* vol. 182, and other volumes in this series; and manufacturer's literature on use of protein purification products, e.g., Pharmacia, Piscataway, N.J., or Bio-Rad, Richmond, Calif. Combination with recombinant techniques allow fusion to appropriate segments (epitope tags), e.g., to a FLAG sequence or an equivalent which can be fused, e.g., via a protease-removable sequence. See, e.g., Hochuli (1989) *Chemische Industrie* 12:69–70; Hochuli (1990) "Purification of Recombinant Proteins with Metal Chelate Absorbent" in Setlow (ed.) *Genetic Engineering, Principle and Methods* 12:87–98, Plenum Press, NY; and Crowe, et al. (1992) *QIAexpress: The High Level Expression & Protein Purification System* QUIAGEN, Inc., Chatsworth, Calif.

Standard immunological techniques are described, e.g., in Coligan (1991) *Current Protocols in Immunology* Wiley/Greene, NY; and *Methods in Enzymology* volumes. 70, 73, 74, 84, 92, 93, 108, 116, 121, 132, 150, 162, and 163. Assays for neural cell biological activities are described, e.g., in Wouterlood (ed. 1995) *Neuroscience Protocols* modules 10, Elsevier; *Methods in Neurosciences* Academic Press; and *Neuromethods* Humana Press, Totowa, N.J. Methodology of developmental systems is described, e.g., in Meisami (ed.) *Handbook of Human Growth and Developmental Biology* CRC Press; and Chrispeels (ed.) *Molecular Techniques and Approaches in Developmental Biology* Interscience.

FACS analyses are described in Melamed, et al. (1990) *Flow Cytometry and Sorting* Wiley-Liss, Inc., New York, N.Y.; Shapiro (1988) *Practical Flow Cytometry* Liss, New York, N.Y.; and Robinson, et al. (1993) *Handbook of Flow Cytometry Methods* Wiley-Liss, New York, N.Y.

II. Isolation of CCL28 or CCL27 Chemokine Clone

A clone encoding the CCL28 or CCL27 chemokine is isolated from a natural source by many different possible methods. Given the sequences provided herein, PCR primers or hybridization probes are selected and/or constructed to isolate either genomic DNA segments or cDNA reverse transcripts. Appropriate cell sources include listed tissues, e.g., skin or epithelial or wound healing libraries. Genetic and polymorphic or allelic variants are isolated by screening a population of individuals.

PCR based detection is performed by standard methods, preferably using primers from opposite ends of the coding sequence, but flanking segments might be selected for specific purposes.

Alternatively, hybridization probes are selected. Particular AT or GC contents of probes are selected depending upon the expected homology and mismatching expected. Appropriate stringency conditions are selected to balance an appropriate positive signal to background ratio. Successive washing steps are used to collect clones of greater homology.

Further clones are isolated using an antibody based selection procedure. Standard expression cloning methods are applied including, e.g., FACS staining of membrane associated expression product. The antibodies are used to identify clones producing a recognized protein. Alternatively, antibodies are used to purify a CCL28 or CCL27 chemokine, with protein sequencing and standard means to isolate a gene encoding that protein.

Genomic sequence based methods will also allow for identification of sequences naturally available, or otherwise, which exhibit homology to the provided sequences.

III. Isolation of a Primate Counterpart for Chemokine Clone

Similar methods are used as above to isolate an appropriate primate chemokine gene from another primate. Similar source materials are used to isolate natural genes, including genetic, polymorphic, allelic, or strain variants. Other species variants are also isolated using similar methods. Alternatively, gene databases may be searched for the appropriate motifs.

IV. Isolation of a Rodent Chemokine Clone

An appropriate rodent source is selected as above, e.g., rat, hamster, etc. Similar methods are utilized to isolate a species variant, though the level of similarity will typically be lower for rodent chemokine as compared to a human to other primate sequence.

V. Chromosomal Localization

The cDNA is labeled, e.g., nick-translated with biotin-14 dATP and hybridized in situ at a final concentration of 5 ng/μl to metaphases from two normal animals, preferably males. Fluorescence in situ hybridization (FISH) method may be modified from that described by Callen, et al. (1990). *Ann. Genet.* 33:219–221, in that chromosomes are stained before analysis with both propidium iodide (as counter stain) and DAPI (for chromosome identification). Images of metaphase preparations are captured by a CCD camera and computer enhanced. Identification of the appropriate labeled chromosomes is determined. Localization to the standard locations for such molecule, or different location may also provide information as to function.

The human CCL28 has been localized to human chromosome 9p13.

VI. Expression; Purification; Characterization

With an appropriate clone from above, the coding sequence is inserted into an appropriate expression vector. This may be in a vector specifically selected for a prokaryote, yeast, insect, or higher vertebrate, e.g., mammalian expression system. Standard methods are applied to produce the gene product, preferably as a soluble secreted molecule, but will, in certain instances, also be made as an intracellular protein. Intracellular proteins typically require cell lysis to recover the protein, and insoluble inclusion bodies are a common starting material for further purification.

With a clone encoding a CCL28 or CCL27 chemokine, recombinant production means are used, although natural forms may be purified from appropriate sources. The protein product is purified by standard methods of protein purification, in certain cases, e.g., coupled with immunoaffinity methods. Immunoaffinity methods are used either as a purification step, as described above, or as a detection assay to determine the separation properties of the protein.

Preferably, the protein is secreted into the medium, and the soluble product is purified from the medium in a soluble form. Alternatively, as described above, inclusion bodies from prokaryotic expression systems are a useful source of material. Typically, the insoluble protein is solubilized from the inclusion bodies and refolded using standard methods. Purification methods are developed as described above.

The product of the purification method described above is characterized to determine many structural features. Standard physical methods are applied, e.g., amino acid analysis and protein sequencing. The resulting protein is subjected to CD spectroscopy and other spectroscopic methods, e.g., NMR, ESR, mass spectroscopy, etc. The product is characterized to determine its molecular form and size, e.g., using gel chromatography and similar techniques. Understanding of the chromatographic properties will lead to more gentle or efficient purification methods.

Prediction of glycosylation sites may be made, e.g., as reported in Hansen, et al. (1995) *Biochem. J.* 308:801–813.

VII. Preparation of Antibodies against Chemokines

With DNA for expression, or protein produced, e.g., as above, animals are immunized to produce antibodies. Polyclonal antiserum is raised, in some cases, using non-purified antigen, though the resulting serum will exhibit higher background levels. Preferably, the antigen is purified using standard protein purification techniques, including, e.g., affinity chromatography using polyclonal serum indicated above. Presence of specific antibodies is detected using defined synthetic peptide fragments.

Polyclonal serum is raised against a purified antigen, purified as indicated above, or using, e.g., a plurality of, synthetic peptides. A series of overlapping synthetic peptides which encompass all of the full length sequence, if presented to an animal, will produce serum recognizing most linear epitopes on the protein. Such an antiserum is used to affinity purify protein, which is, in turn, used to introduce intact full length protein into another animal to produce another antiserum preparation.

Similar techniques are used to generate induce monoclonal antibodies to either unpurified antigen, or, preferably, purified antigen. The antiserum or antibodies may recognize native protein, or may recognize denatured antigen. The preparations may be immunoselected, or immunopurified, as desired.

Polypeptide fragments corresponding to amino acid residues about 31–41, about 52–63, and about 77–98, of SEQ ID NO:6 (CCL27), have an unusually high antigenicity, according to Parker antigenicity analysis using MacVector 7.1® from Accelrys, Inc. (San Diego, Calif.). A Welling antigenicity plot revealed that regions of unusual antigenicity to be fragments comprising amino acids 39–41, about 58–72, and about 90–100 of SEQ ID NO:6, with analysis using MacVector 7.1®. It is contemplated to use one or more of these antigenic regions, or a fragment of one or more of these antigenic regions, for antibody production. It is not intended to limit the invention to the use of the described regions and fragments for the production of antibodies.

Polypeptide fragments corresponding to amino acid residues of unusual antigenicity to be fragments comprising amino acids 28–38, 48–51, 70–84, 84–122, and 70–122 of SEQ ID NO:2 (CCL28), according to Parker antigenicity analysis using MacVector 7.1® from Accelrys, Inc. (San Diego, Calif.). A Welling antigenicity plot revealed regions of unusual antigenicity to be 10–20, 37–42, 61–68, and 95–122, with analysis by MacVector 7.10®. It is contemplated to use one or more of these antigenic regions, or a fragment of one or more of these antigenic regions, for antibody production. It is not intended to limit the invention to the use of the described regions and fragments for the production of antibodies.

Antibodies to CCL28 were prepared against three separate peptides, where the peptides were synthesized using the predicted amino acid sequence of CCL28 and used in immunoblotting studies (WO 99/36540 to Papsidero, et al., pp. 48–51).

VIII. Cellular and Tissue Distribution

Distribution of the protein or gene products are determined, e.g., using immunohistochemistry with an antibody reagent, as produced above, or by screening for nucleic acids encoding the chemokine. Hybridization or PCR methods are used to detect DNA, cDNA, or message content. Histochemistry allows determination of the specific cell types within a tissue which express higher or lower levels of message or DNA. Antibody techniques are useful to quantitate protein in a biological sample, including a liquid or tissue sample. Immunoassays are developed to quantitate protein. Also, FACS analysis may be used to evaluate expression in a cell population.

The mouse CCL27 sequence has been detected in fetal mouse, 1 sequence from 14.5 days post conception, and 3 sequences from 19.5 days post conception. Three sequences have come from adult mouse, 1 each from liver, placenta, and skin. Northern analysis shows signal in testes is much greater than that in brain, which is much greater than that in lung.

CCL27 occurs in the outermost cell layers of murine skin, corresponding to the epidermis, and only rarely in cells of the dermis, according to immunohistological analysis (Morales, et al. (1999) *Proc. Natl. Acad. Sci. USA* 96:14470–14475). In skin from healthy human donors, epidermal keratinocytes contain detectable CCL27, where the most abundant expression occurs in keratinocytes in the basal layers of the epidermis, and lower levels in keratinocytes of suprabasal layers, according to immunohistogical analysis (Homey, et al. (2002) *Nature Med.* 8:157–165). Other studies of human skin revealed that CCL27 is expressed in skin, but not other tissues, where analysis was by Northern blots (Pan, et al. (2000) *J. Immunol.* 165: 2943–2949). CCL27 is also expressed in macrophages, dendritic cells, and other cells.

In mouse, CCL27 takes two forms, where one bears a signal peptide, while the other form appears to localize in the nucleus (Baird, et al. (1999) *J. Biol. Chem.* 274:33496–33503).

Total RNA was isolated from a variety of cell types and tissues using RNEasy® mini kit from Qiagen (Valencia, Calif.) using the manufacturer's suggested protocols. RNA was reverse transcribed using oligo dT primers, and Multiscribe® reverse transcriptase (Perkin Elmer Applied Biosystems, Foster City, Calif.), according to the manufacturer's protocols. cDNA was analyzed for the expression of CCL27, using ubiquitin expression as a standard. cDNA was analyzed for the expression of CCL27 (CCL27) and CCR10 genes using a Perkin-Elmer ABI Prism® 7700 Sequence Detection System (Perkin-Elmer Applied Biosystems, Foster City, Calif.). Amplification of cDNA was by Taqman® PCR assay for real-time quantitative PCR (Perkin-Elmer Applied Biosystems, Foster City, Calif.). Quantitation of expression of target genes was calculated by normalizing the values relative to the expression of ubiquitin.

Results of Taqman® analysis are presented in Table 1

| Human cell type | Human CCL27 |
| --- | --- |
| Epithelial cell keratinocyte untreated | (++) |
| Epithelial cell keratinocyte activated TNFα + IL-1 | (+++) |
| Keratinocytes, untreated | (+) |
| Keratinocytes; TNF-α/IL-1β + IL-10, 18 hours | (++) |
| Keratinocytes; TNF-α/IL-1β, 18 hours | (+++) |
| Keratinocytes; IL-4, 18 hours | (+) |
| Keratinocytes; IFN-γ, 18 hours | (+) |

| Mouse cell or tissue type | Mouse CCL27 |
| --- | --- |
| Fibroblast cell resting L cell line | (−) |
| Dendritic cell resting ex spleen | (+, −) |
| Dendritic cell resting ex bone marrow | (+++) |
| Macrophage resting ex bone marrow | (+++) |
| Macrophage activated LPS + IFNγ + anti-IL-10R ex bone marrow | (++) |
| Mesenteric lymph nodes IL-10 knockout treated IL-10 | (+++) |
| Mesenteric lymph nodes IL-10 knockout treated αIL-12 | (+) |

Distribution of CCL28 and Association with Inflammation (GVHD) and Cancer.

CCL28 is expressed in the entire gastrointestinal tract, trachea, placenta, pancreas, thyroid gland, salivary glands, and mammary glands, as determined by a Clontech human multiple tissue expression (MTE®) array RNA blot (BD Clontech, Palo Alto, Calif.) (WO 01/92301 of Hromas, pp. 84–85). Immunohistological analysis revealed CCL28 to occur in human colon, and induced in the colon of patients who had developed graft versus host disease after allogeneic bone marrow transplantation (WO 01/92301 of Hromas, pp. 84–85).

Northern blot analysis of human tissues revealed that CCL28 is predominantly expressed in prostate, colon, spleen, and to a lesser degree in peripheral blood leukocytes. Analysis of murine tissues revealed that CCL28 is expressed mainly in the testis, and to a lesser degree in kidney and brain (Wang, et al. (2000) *J. Biol. Chem.* 275:22313–22323).

Taqman® analysis was used for tissues and cell lines with limited levels of mRNA. Mouse CCL28 was expressed in colon, colon from IL-10 knockout mouse, lung, rag-1 liver, or normal thymus. Mouse CCL28 was expressed in stomach of IL-10 knockout mouse, but not in stomach of normal mouse. Mouse CCL28 was expressed in Th1-type T cells, but not in Th2-type T cells (FIG. 5 in Wang, et al. (2000) *J. Biol. Chem.* 275:22313–22323).

Taqman analysis of human samples revealed CCL28 to be expressed in psoriatic skin and normal skin, where expression was about 20-fold greater in psoriatic skin. CCL28 was expressed in normal thyroid, Hashimoto's thyroidosis thyroid sample, normal colon, ulcerative colitis colon, and eosinophils, but not in inflamed tonsil, fetal heart, fetal brain, fetal liver, or various sources of dendritic cells, B cells, T cells, or unfractionated white blood cells from blood (PBMCs) (FIG. 6 in Wang, et al. (2000) *J. Biol. Chem.* 275:22313–22323).

A polyclonal antibody against a 20-amino acid peptide (residues 78–98) of murine CCL28 was prepared in rabbits (Zymed Laboratories, Inc., South San Francisco, Calif.). The anti-CCL28 antibody was used for immunohistological analysis of tissue samples, such as mouse gut. Immunohistological analysis of the intestines revealed CCL28 to be present in the epithelial cells (Wang, et al. (2000) *J. Biol. Chem.* 275:22313–22323).

CCL28 expression is high in many normal human breast samples, with lower expression in other epithelial-enriched tissues, such as salivary gland, colon, and prostate, with analysis by Northern blots. CCL28 expression is reduced or eliminated in most human breast tumors, as compared to normal adjacent tissues. In situ hybridization confirms the above finding (Mickanin, et al. (2001) *Int. J. Oncol.* 18:939–944).

CCL28 levels in human blood serum were measured using antibodies raised against peptides from MACK. Only serum from patients with breast cancer provided a positive signal, and here the immunoblot method revealed two protein bands, at 20–30 kDa and 7–12 kDa. Of 31 blood samples from patients with breast cancer tested, one specimen showed only the 20–30 kDa forms, while all others showed both forms. None of the ten serum specimens from patients with prostate, ovarian, lung, or colon cancer gave a positive signal, and none of the serum samples from seven normal patients gave a positive signal. (WO 99/36540 of Papsidero, et al., pp. 49–51).

IX. Microchemotaxis Assays

The pro-migratory activities of CCL27 chemokine are assessed in microchemotaxis assays. See, e.g., Bacon, et al. (1988) *Br. J. Pharmacol.* 95:966–974. Other trafficking assays are also used. See, e.g., Quidling-Järbrink, et al. (1995) *Eur. J. Immunol.* 25:322–327; Koch, et al. (1994) *J. Clinical Investigation* 93:921–928; and Antony, et al. (1993) *J. Immunol.* 151:7216–7223.

Chemokines may also be assayed for activity in hemopoietic assays as described, e.g., by H. Broxmeyer. See Bellido, et al. (1995) *J. Clinical Investigation* 95:2886–2895; and Jilka, et al. (1995) *Exptl Hematology* 23:500–506. They may be assayed for angiogenic activities as described, e.g., by Streiter, et al. (1992) *Am. J. Pathol.* 141:1279–1284. Or for a role in inflammation. See, e.g., Wakefield, et al. (1996) *J. Surgical Res,* 64:26–31.

Chemotaxis in response to CCL27 gradients was measured using human white blood cells. The identities of migrating and non-migrating cells were determined by labeled antibodies that recognized various membrane-bound proteins. CCL27 stimulated chemotaxis of $CD4^+$, $CLA^+$ memory T cells, but not of $CD4^+$, $CLA^-$ memory T cells.

CCL27 was also chemotactic toward CD8+, CLA+ memory T cells, but not to CD8+, CLA− memory T cells. CCL27 was not chemotactic to naive T cells, B cells, monocytes, or neutrophils (Morales, et al. (1999) *Proc. Natl. Acad. Sci. USA* 96:14470–14475; WO 00/38713).

Injection of CCL27 into the skin attracts lymphocytes, as shown by histological analysis (FIG. 5f of Homey, et al. (2002) supra). Analysis of mRNA expression in skin tissue by real time PCR revealed that the CCL27 skin injection also resulted in increased levels of mRNA coding for IL-2, CCR10, and the α-chain of LFA (LFA-1α), indicating increased recruitment of T cells to the site of injection (FIG. 5g of Homey, et al. (2002) supra; WO 00/38713).

The correlation between CCL27 response and the presence of CLA is consistent with the finding that only about 5% of T cells in non-inflamed skin express CLA, while most of the T cells of inflamed skin express CLA (Homey, et al. (2000) *Nature Med.* 8:157–165).

A study of mouse genomic DNA revealed that the mouse genome contains two different CCL27 genes. One of these genes is deleted in the plt strain of mice, a strain with abnormalities in white blood cell migration and immune response (Nakano and Gunn (2001) *J. Immunol.* 166:361–369). The results from the plt strain of mice implicate CCL27 as a modulator of leukocyte migration.

Treatment of unfractionated white blood cells (peripheral blood mononuclear cells, PBMC) with CCL27 results in increased expression of CD3 and CD4 (Table I of Baird, et al. (1999) *J. Biol. Chem.* 274:33496–33503). CD3 and CD4 are membrane-bound proteins of T cells that play a central role in T cell activation (Abbas, et al. (2000) *Cellular and Molecular Immunology*, 4$^{th}$ ed., W. B. Saunders Col, Philadelphia, Pa.). CD3 and CD4 are also commonly used as markers for T cells. Thus, CCL27's effect on T cells includes types of cell activation that are not directly related to migration.

Note that CD3 and CD4 also occur on certain subpopulations of macrophages and NK cells (Hewson, et al. (2001) *J. Immunol.* 166:4835–4842; Arase, et al. (2001) *J. Immunol.* 166:21–25; Toyama-Sorimachi, et al. (2001) *J. Immunol.* 166:3771–3779). Hence, the results of the effect of CCL27 on PBMCs may be due, in part, to activation of macrophages or NK cells. Exposing keratinocytes to TNF-α plus IL-1β results in a marked induction of CCL27 mRNA (FIG. 3 of Morales, et al. (1999) *Proc. Natl. Acad. Sci. USA* 96:14470–14475). This induction of CCL27 by TNF-α plus IL-1 suggests a role of CCL27 in skin inflammation, because TNF-α and IL-1β both increase skin inflammation. The relevance of these two cytokines to skin inflammation was demonstrated by the use of anti-TNF-α (Iyer, et al. (2002) *Br. J. Dermatol.* 146:118–121) and anti-IL-1β (Schon, et al. (2001) *Clin. Exp. Immunol.* 123:505–510) in the treatment of psoriasis.

Human CCL28 attracts resting CD4+ T cells and resting CD8+ T cells. T cells activated with anti-CD3 antibody did not respond to CCL28. Human CCL28 is was found not to be chemotactic towards T cells bearing the β7 polypeptide chain. Maximal chemotaxis of T cells was specifically found at 100–200 nM CCL28 (Wang, et al. (2000) *J. Biol. Chem.* 275:22313–22323).

Transfectant cells bearing CCR10 are attracted by CCL28, as well as by another chemokine, CCL27. However, transfectant cells bearing CCR3 are attracted by CCL28, but not by CCL27 (Pan, et al. (2000) supra). CCL28 is chemotactic towards T cells, where one subpopulation of T cells that is attracted is CD45R$^{lo}$CLA$^{hi}$ T cells (FIG. 2B of Pan, et al. (2000) supra). CCL28 is also chemotactic towards eosinophils (FIG. 2C of Pan, et al. (2000) supra). CCL28 is not chemotactic towards naive or memory blood B cells. Eosinophils, which naturally express CCR3, are attracted by CCL28. Migration of eosinophils towards CCL28 was blocked by a monoclonal antibody towards the receptor, CCR3. Hence, CCL27 and CCL28 differ functionally in that CCL27 attracts cells bearing CCR10, while CCL28 attracts cells bearing CCR10 and cells bearing CCR3 (Pan, et al. (2000) supra).

X. Biological Activities, Direct and Indirect

A robust and sensitive assay is selected as described above, e.g., on immune cells, neuronal cells, or stem cells. Chemokine is added to the assay in increasing doses to see if a dose response is detected. For example, in a proliferation assay, cells are plated out in plates. Appropriate culture medium is provided, and chemokine is added to the cells in varying amounts. Growth is monitored over a period of time which will detect either a direct effect on the cells, or an indirect effect of the chemokine.

Alternatively, an activation assay or attraction assay is used. An appropriate cell type is selected, e.g., hematopoietic cells, myeloid (macrophages, neutrophils, polymorphonuclear cells, etc.) or lymphoid (T cell, B cell, or NK cells), neural cells (neurons, neuroglia, oligodendrocytes, astrocytes, etc.), or stem cells, e.g., progenitor cells which differentiate to other cell types, e.g., gut crypt cells and undifferentiated cell types.

Other assays will be those which have been demonstrated with other chemokines. See, e.g., Schall and Bacon (1994) *Current Opinion in Immunology* 6:865–873; and Bacon and Schall (1996) *Int. Arch. Allergy & Immunol.* 109:97–109.

XI. Structure Activity Relationship

Information on the criticality of particular residues is determined using standard procedures and analysis. Standard mutagenesis analysis is performed, e.g., by generating many different variants at determined positions, e.g., at the positions identified above, and evaluating biological activities of the variants. This may be performed to the extent of determining positions which modify activity, or to focus on specific positions to determine the residues which can be substituted to either retain, block, or modulate biological activity.

Alternatively, analysis of natural variants can indicate what positions tolerate natural mutations. This may result from populational analysis of variation among individuals, or across strains or species. Samples from selected individuals are analyzed, e.g., by PCR analysis and sequencing. This allows evaluation of population polymorphisms.

XII. Screening for Agonists/Antagonists

Agonists or antagonists are screened for ability to induce or block biological activity. The candidate compounds, e.g., sequence variants of natural CCL27 chemokine, are assayed for their biological activities. Alternatively, compounds are screened, alone or in combinations, to determine effects on biological activity.

XIII. Isolation of a Receptor for Chemokine

A CCL28 or CCL27 chemokine can be used as a specific binding reagent to identify its binding partner, by taking advantage of its specificity of binding, much like an antibody would be used. A binding reagent is either labeled as described above, e.g., fluorescence or otherwise, or immobilized to a substrate for panning methods. The typical chemokine receptor is a seven transmembrane receptor.

The binding composition, e.g., chemokine, is used to screen an expression library made from a cell line which expresses a binding partner, i.e. receptor. Standard staining techniques are used to detect or sort intracellular or surface expressed receptor, or surface expressing transformed cells are screened by panning. Screening of intracellular expression is performed by various staining or immunofluorescence procedures. See also McMahan, et al. (1991) *EMBO J.* 10:2821–2832.

Standard $Ca^{++}$ flux protocols, see, e.g., Coligan, et al. (eds.)(1992 and periodic supplements) *Current Protocols in Immunol.* Greene/Wiley, New York, N.Y., can be used to identify a receptor for CCL27.

For example, on day 0, precoat 2-chamber permanox slides with 1 ml per chamber of fibronectin, 10 ng/ml in PBS, for 30 min at room temperature. Rinse once with PBS. Then plate COS cells at $2-3\times10^5$ cells per chamber in 1.5 ml of growth media. Incubate overnight at 37° C.

On day 1 for each sample, prepare 0.5 ml of a solution of 66 µg/ml DEAE-dextran, 66 µM chloroquine, and 4 µg DNA in serum free DME. For each set, a positive control is prepared, e.g., of human CCL27 chemokine cDNA at 1 and 1/200 dilution, and a negative mock. Rinse cells with serum free DME. Add the DNA solution and incubate 5 hr at 37° C. Remove the medium and add 0.5 ml 10% DMSO in DME for 2.5 min. Remove and wash once with DME. Add 1.5 ml growth medium and incubate overnight.

On day 2, change the medium. On days 3 or 4, the cells are fixed and stained. Rinse the cells twice with Hank's Buffered Saline Solution (HBSS) and fix in 4% paraformaldehyde (PFA)/glucose for 5 min. Wash 3× with HBSS. The slides may be stored at –80° C. after all liquid is removed. For each chamber, 0.5 ml incubations are performed as follows. Add HBSS/saponin (0.1%) with 32 µl/ml of 1 M $NaN_3$ for 20 min. Cells are then washed with HBSS/saponin 1×. Add chemokine or chemokine/antibody complex to cells and incubate for 30 min. Wash cells twice with HBSS/saponin. If appropriate, add first antibody for 30 min. Add second antibody, e.g., Vector anti-mouse antibody, at 1/200 dilution, and incubate for 30 min. Prepare ELISA solution, e.g., Vector Elite ABC horseradish peroxidase solution, and preincubate for 30 min. Use, e.g., 1 drop of solution A (avidin) and 1 drop solution B (biotin) per 2.5 ml HBSS/saponin. Wash cells twice with HBSS/saponin. Add ABC HRP solution and incubate for 30 min. Wash cells twice with HBSS, second wash for 2 min, which closes cells. Then add Vector diaminobenzoic acid (DAB) for 5 to 10 min. Use 2 drops of buffer plus 4 drops DAB plus 2 drops of $H_2O_2$ per 5 ml of glass distilled water. Carefully remove chamber and rinse slide in water. Air dry for a few minutes, then add 1 drop of Crystal Mount and a cover slip. Bake for 5 min at 85–90° C.

Evaluate positive staining of pools and progressively subclone to isolation of single genes responsible for the binding.

Alternatively, chemokine reagents are used to affinity purify or sort out cells expressing a receptor. See, e.g., Sambrook, et al. or Ausubel, et al.

Another strategy is to screen for a membrane bound receptor by panning. The receptor cDNA is constructed as described above. The ligand can be immobilized and used to immobilize expressing cells. Immobilization may be achieved by use of appropriate antibodies which recognize, e.g., a FLAG sequence of a chemokine fusion construct, or by use of antibodies raised against the first antibodies. Recursive cycles of selection and amplification lead to enrichment of appropriate clones and eventual isolation of receptor expressing clones.

Phage expression libraries can be screened by chemokine. Appropriate label techniques, e.g., anti-FLAG antibodies, will allow specific labeling of appropriate clones.

A receptor for CCL27 and CCL28 was identified by screening a panel of known and orphan chemokine from human and murine sources. A positive-screening receptor was identified by calcium flux assays, using mouse cells transfected with the above-mentioned receptors. This receptor is CCR10 (a.k.a. GPR2). Human CCL28 produced a positive signal with mouse cells transfected with human CCR10 or with mouse CCR10 (Wang, et al. (2000) *J. Biol. Chem.* 275:22313–22323).

XIV. Immunohistochemical Localization

The antibody described above is used to identify expression of CCL28 or CCL27 in various tissues. Methods for immunohistochemical staining are described, e.g., in Sheehan, et al. (eds.) (1987) *Theory and Practice of Histotechnology*, Battelle Press, Columbus, Ohio.

XV. Contact Allergy and Psoriasis in Humans, Increase in CCL27 Levels, and Increase in Cells Bearing CCL27 Receptor CCL27 was found in skin of healthy subjects, where it occurs in basal keratinocytes of the basal layer, and in endothelial cells of the superficial dermal plexus. With nickel exposure, CCL27 levels increased in the epidermal keratinocytes of the basal and suprabasal layers, as well as in the dermis (unexposed skin showed only weak expression of CCL27 in the dermis) (FIG. 2 of Homey, et al. (2002) *Nature Med.* 8:157–165).

CCL27 receptor was not detected in the epidermis of skin from healthy subjects, though it was found in scattered cells of the superficial dermal plexus. The weak expression in the dermis of normal skin corresponded to $CD31^+$ endothelial cells.

With nickel exposure, skin was invaded by lymphocytes bearing CCL27 receptor, and strong CCL27 receptor signals were found in the perivascular, subepidermal, and intraepidermal regions (FIG. 2 of Homey, et al. (2002) *Nature Med.* 8:157–165). These results support a role for CCL27 to CCR10 interactions in modulating human skin disease states.

As mentioned above, CCL27 receptor is not readily detected in healthy epidermis. However, lesional skin from patients with psoriasis or atopic dermatitis showed strong CCL27 receptor expression, where expression was located on lymphocytes (FIG. 1 of Homey, et al. (2002) *Nature Med.* 8:157–165). These results support a role for CCL27 to CCR10 interactions in modulating human skin disease states.

XVI. Animal Models of Allergies and Treatment with Anti-CCL27 Antibodies

An animal model of contact allergy can be produced by dinitrofluorobenzene (DNF). DNF treatment provoked an increase in CCL27 levels in skin, and infiltration of white blood cells, and swelling. Treatment with anti-CCL27 antibody resulted in a reduction of skin swelling. Anti-CCL27 antibodies were from R & D Systems, Minneapolis, Minn.

An animal model of chronic atopic dermatis can be produced by ovalbumin treatment. Ovalbumin treatment results in infiltration of $CD4^+$ lymphocytes in the skin, with some infiltration by eosinophils. CCL27 is present in keratinocytes of normal mice, as determined by histological analysis. Ovalbumin-induced skin swelling and inflammation was reduced by anti-CCL27 antibodies, where lymphocyte recruitment was reduced by 90%. Anti-CCL27 antibody seemed not to change eosinophil levels, however, demonstrating specificity of anti-CCL27 action (FIG. 6 of Homey, et al. (2002) *Nature Med.* 8:157–165).

All references cited herein are incorporated herein by reference to the same extent as if each individual publication or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

TABLE 2

| Description of SEQ ID NOs. | |
| --- | --- |
| Sequence Identifier | Sequence |
| SEQ ID NO: 1 | human CCL28 nucleic acid sequence |
| SEQ ID NO: 2 | human CCL28 polypeptide sequence |
| SEQ ID NO: 3 | human CCL28 nucleic acid sequence |

TABLE 2-continued

| Description of SEQ ID NOs. | |
| --- | --- |
| Sequence Identifier | Sequence |
| SEQ ID NO: 4 | human CCL28 nucleic acid sequence |
| SEQ ID NO: 5 | hCCL27 nucleic acid sequence |
| SEQ ID NO: 6 | hCCL27 amino acid sequence |
| SEQ ID NO: 7 | mCCL27 nucleic acid sequence |
| SEQ ID NO: 8 | mCCL27 amino acid sequence |
| SEQ ID NO: 9 | human MCP-1 polypeptide sequence |
| SEQ ID NO: 10 | human MIP-3α polypeptide sequence |
| SEQ ID NO: 11 | longer transcript with human CCL28 |
| SEQ ID NO: 12 | longer polypeptide with human CCL28 |

What is claimed is:

1. An isolated polypeptide comprising the amino acid sequence of SEQ ID NO: 6 or an antigenic fragment comprising 10 or more contiguous amino acids thereof.

2. The polypeptide of claim 1 comprising 20 contiguous amino acids of SEQ ID NO: 6.

3. The polypeptide of claim 2 comprising 30 contiguous amino acids of SEQ ID NO: 6.

4. A pharmaceutical composition comprising the polypeptide of claim 1 in conjunction with a suitable carrier.

5. A method of producing a polypeptide of claim 1 comprising culturing a host cell comprising a polynucleotide encoding said polypeptide under conditions suitable for the expression of said polypeptide and recovering the polypeptide from the culture.

6. The polypeptide of claim 1 bound to human CCR10.

7. The polypeptide of claim 3 comprising 50 contiguous amino acids of SEQ ID NO: 6.

8. The polypeptide of claim 7 comprising 70 contiguous amino acids of SEQ ID NO: 6.

9. An isolated polypeptide comprising the amino acid sequence of SEQ ID NO: 6.

* * * * *